United States Patent
Nojiri et al.

(10) Patent No.: US 11,304,879 B2
(45) Date of Patent: Apr. 19, 2022

(54) ADHESIVE COMPOSITION FOR DENTAL USE

(71) Applicant: KURARAY NORITAKE DENTAL INC., Kurashiki (JP)

(72) Inventors: Yamato Nojiri, Niigata (JP); Naoki Nishigaki, Niigata (JP); Mitsunobu Kawashima, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 31 days.

(21) Appl. No.: 17/048,799

(22) PCT Filed: Apr. 19, 2019

(86) PCT No.: PCT/JP2019/016874
§ 371 (c)(1),
(2) Date: Oct. 19, 2020

(87) PCT Pub. No.: WO2019/203356
PCT Pub. Date: Oct. 24, 2019

(65) Prior Publication Data
US 2021/0145701 A1     May 20, 2021

(30) Foreign Application Priority Data
Apr. 20, 2018    (JP) .............................. JP2018-081758

(51) Int. Cl.
*A61K 6/30*      (2020.01)
*C08L 43/02*     (2006.01)

(52) U.S. Cl.
CPC ............... *A61K 6/30* (2020.01); *C08L 43/02* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 4,719,297 A | 1/1988 | Henne et al. | |
| 5,064,495 A * | 11/1991 | Omura ................. | C09J 4/00 156/307.3 |
| 5,186,783 A * | 2/1993 | Kawashima ........... | C09J 4/00 156/307.3 |
| 5,254,198 A * | 10/1993 | Kawashima ........... | C09J 4/00 156/307.3 |
| 5,866,631 A * | 2/1999 | Nakagawa ............. | A61K 6/71 523/118 |
| 5,925,690 A * | 7/1999 | Fuchigami ............. | A61K 6/76 523/118 |
| 6,458,868 B1 * | 10/2002 | Okada .................. | C07F 9/098 523/116 |
| 2003/0171450 A1 * | 9/2003 | Wang .................... | A61K 6/40 523/115 |
| 2004/0077746 A1 * | 4/2004 | Takeshita ............... | A61K 6/30 523/116 |
| 2004/0254261 A1 * | 12/2004 | Kojima .................. | A61K 6/30 523/118 |
| 2006/0135719 A1 * | 6/2006 | Moszner ................ | A61K 6/887 526/303.1 |
| 2010/0041790 A1 | 2/2010 | Moszner et al. | |
| 2011/0288195 A1 * | 11/2011 | Kajikawa ............... | A61K 6/887 522/11 |
| 2012/0202913 A1 * | 8/2012 | Kawana ................. | A61K 6/54 522/84 |
| 2015/0190313 A1 * | 7/2015 | Inaki ..................... | A61K 6/30 523/118 |
| 2016/0106519 A1 * | 4/2016 | Hashiguchi ............ | A61C 5/50 206/222 |
| 2017/0071699 A1 * | 3/2017 | Yamashita ............. | B65D 47/12 |
| 2017/0156991 A1 * | 6/2017 | Shimizu ................. | A61K 6/30 |
| 2017/0253555 A1 * | 9/2017 | Inaki ..................... | C07C 67/26 |
| 2021/0145701 A1 * | 5/2021 | Nojiri ..................... | A61K 6/30 |

FOREIGN PATENT DOCUMENTS

| EP | 0 009 348 B1 | 7/1983 |
|---|---|---|
| JP | 57-167364 A | 10/1982 |
| JP | 57-197289 A | 12/1982 |
| JP | 2001-39992 A | 2/2001 |

(Continued)

OTHER PUBLICATIONS

IP.com U.S. Appl. No. 17/048,799 (Year: 2021).*

(Continued)

*Primary Examiner* — Peter A Salamon
(74) *Attorney, Agent, or Firm* — Oblon, McClelland, Maier & Neustadt, L.L.P.

(57) ABSTRACT

The present invention provides a dental adhesive composition that, even after photocuring with a high-output LED irradiator, shows high bond strength not only for dentin untreated by phosphoric acid etching but also for dentin treated by phosphoric acid etching. The present invention relates to a dental adhesive composition comprising a phosphoric acid group-containing polymerizable monomer (A), the phosphoric acid group-containing polymerizable monomer (A) comprising: a dihydrogen phosphate monoester group-containing polymerizable monomer (A-1) represented by general formula (1); a hydrogen phosphate diester group-containing polymerizable monomer (A-2) represented by general formula (2); and a phosphoric acid tetraester group-containing polymerizable monomer (A-3) represented by general formula (3).

7 Claims, No Drawings

(56) References Cited

FOREIGN PATENT DOCUMENTS

| | | |
|---|---|---|
| JP | 2006-176522 A | 7/2006 |
| JP | 2012-193152 A | 10/2012 |
| JP | 2014-55115 A | 3/2014 |
| JP | 2015-44761 A | 3/2015 |
| JP | 2015-67551 A | 4/2015 |

OTHER PUBLICATIONS

Google scholar search (Year: 2021).*
International Search Report dated Jun. 4, 2019 in PCT/JP2019/016874 filed Apr. 19, 2019, citing documents AA-AB, AN-AS and AX therein, 2 pages.
Yaguchi, T., "Layering mechanism of MDP-Ca salt produced in demineralization of enamel and dentin apatite", ScienceDirect, Dental Materials, vol. 33, 2017, pp. 23-32.

* cited by examiner

ADHESIVE COMPOSITION FOR DENTAL USE

TECHNICAL FIELD

The present invention relates to a dental adhesive composition used in the field of dentistry.

BACKGROUND ART

A restorative filling material such as a filling composite resin or a filling compomer, or a crown restoration material such as a metal alloy, a porcelain, or a resin material is typically used for restoration of tooth structures (enamel, dentin, and cementum) damaged, for example, by dental caries. In general, however, restorative filling materials and crown restoration materials (both of these materials may collectively be referred to as "dental restorative material(s)" in the present specification) themselves have no adhesive property to tooth structures. Traditionally, bonding of a dental restorative material to tooth structure is made with the use of dental adhesive compositions, specifically, dental bonding materials for bonding of restorative filling materials, and dental cements for bonding of crown restoration materials. A variety of adhesive systems are available for bonding of these materials. An example of conventionally-employed adhesive systems is an adhesive system of the so-called acid etching type (total etching type), which includes subjecting the surface of a tooth structure to an etching treatment with an acid etching agent such as an aqueous solution of phosphoric acid, and applying a bonding material—an adhesive in the case of a dental bonding material—for bonding of a dental restorative material to the tooth structure.

Another type of adhesive system is the self-etching type, which does not use an acid etching agent. For years, the mainstream self-etching adhesive system has been a two-step process that includes applying a self-etching primer containing an acidic monomer, a hydrophilic monomer, and water to the surface of a tooth structure, and, without washing with water, applying a bonding material containing a crosslinkable monomer and a polymerization initiator to the tooth structure. Recent years have also seen a widespread use of a one-step self-etching adhesive system that uses a one-pack type dental adhesive (one-pack type bonding material) having functions of both a self-etching primer and a bonding material.

A variant of a self-etching adhesive system is a technique called selective etching, which etches only the enamel with phosphoric acid as a pretreatment for improving adhesive property for enamel. This technique is usually employed when restoring tooth parts that are more dependent on the enamel for bonding, such as the occlusal surface of a molar or the incisal fracture of a front tooth, or when high adhesive property is needed for the enamel. Here, the etching simultaneously processes the dentin at its boundary with the enamel, and, when applied to dentin, which contains organic matter such as collagen, the phosphoric acid etching treatment, because of its generally strong demineralizing effect, is known to severely impair adhesive property by exposing the collagen fibers and causing embrittlement of the dentin structure through demineralization of hydroxyapatite. It is also known that the exposed collagen in the dentin contracts in the process of water washing and drying, and prevents smooth penetration of the polymerizable monomer components contained in the dental adhesive. Indeed, it is difficult with a self-etching dental adhesive to provide high adhesive property for dentin subjected to a phosphoric acid etching treatment, and there is a need for a self-etching material that provides improved adhesive property for dentin after a phosphoric acid etching treatment.

Typically, a dental adhesive composition contains monomer components such as an acidic monomer, a hydrophilic monomer, and a crosslinkable monomer, and (meth)acrylate compounds are commonly used as such monomer components.

The acidic monomer is a polymerizable monomer having an acidic group that chemically binds to the tooth structure for improved adhesive property for the tooth structure, and the acidic group used for this purpose is selected from groups such as a phosphoric acid group, a thiophosphoric acid group, a phosphonic acid group, and a carboxylic acid group. The acidic monomer is used for a wide range of dental adhesive compositions. For improved mechanical strength upon curing of a dental adhesive composition, acidic group-containing polymerizable monomers having a plurality of polymerizable groups have also been used.

For example, Patent Literature 1 proposes a dental adhesive composition containing a dihydrogen phosphate monoester group-containing polymerizable monomer mixed with other components such as a hydrogen phosphate diester group-containing polymerizable monomer and a polyvalent metal alkoxide. It is stated in this related art document that the dental adhesive composition, with these components, provides adhesive property that is strong and stable for both enamel and dentin. Patent Literature 2 proposes a chemical polymerizable dental adhesive composition containing a dihydrogen phosphate monoester group-containing polymerizable monomer mixed with a hydrogen phosphate diester group-containing polymerizable monomer. Patent Literatures 3 and 4 propose a tooth-surface coating material adherent to tooth surface, and a dental polymerizable composition, respectively, containing these polymerizable monomers.

Traditionally, a halogen irradiator has been used as a dental photoirradiator for photocuring of a dental adhesive composition. However, halogen irradiators are being replaced by LED irradiators because of the longer lifetime and higher efficiency of LED. The LED irradiator emits light of a peak wavelength close to that of light emitted by a halogen irradiator. However, the wavelength range is narrower, and the emission spectrum is different. Because of these differences, a photocurable dental material cured with an LED irradiator behaves differently compared to when it is cured with a halogen irradiator. Recent increase in the output of LED irradiators has led to the widespread use of high-output LED irradiators capable of more quickly curing a photopolymerizable resin.

The dental adhesive compositions described in Patent Literatures 1 to 3 exhibit superior photocurability with halogen irradiators and conventional LED irradiators. However, these dental adhesive compositions show only weak bond strength to dentin when subjected to brief irradiation with a high-output LED irradiator, and cannot provide high adhesive property, particularly when used with phosphoric acid etching. Studies by the present inventors also revealed that the dental polymerizable composition of Patent Literature 4 has weak bond strength to dentin when used with phosphoric acid etching involving brief irradiation with a high-output LED irradiator, and requires further improvements.

CITATION LIST

Patent Literature

Patent Literature 1: JP 2015-067551 A
Patent Literature 2: JP 2012-193152 A
Patent Literature 3: JP 2015-044761 A
Patent Literature 4: JP 2001-039992 A

SUMMARY OF INVENTION

Technical Problem

It is accordingly an object of the present invention to provide a dental adhesive composition that, even after photocuring with a high-output LED irradiator, shows high bond strength (initial bond strength and bond durability) not only for dentin untreated by phosphoric acid etching but also for dentin treated by phosphoric acid etching.

Solution to Problem

After further studies, the present inventors found that the foregoing issues can be solved with the use of a specific phosphoric acid group-containing polymerizable monomer, and completed the present invention on the basis of this finding.

Specifically, the present invention includes the following.

[1] A dental adhesive composition comprising a phosphoric acid group-containing polymerizable monomer (A), the phosphoric acid group-containing polymerizable monomer (A) comprising:

a dihydrogen phosphate monoester group-containing polymerizable monomer (A-1) represented by general formula (1);

a hydrogen phosphate diester group-containing polymerizable monomer (A-2) represented by general formula (2); and a phosphoric acid tetraester group-containing polymerizable monomer (A-3) represented by general formula (3),

[Chem. 1]

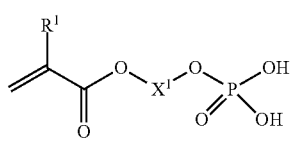
(1)

[Chem. 2]

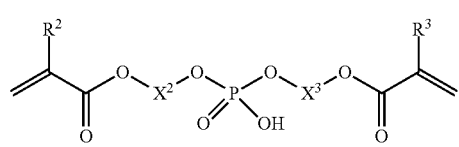
(2)

[Chem. 3]

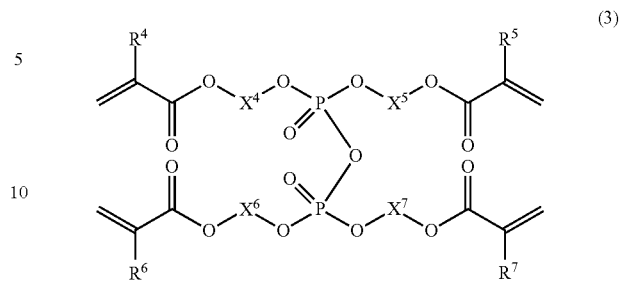
(3)

where $R^1$, $R^2$, $R^3$, $R^4$, $R^5$, $R^6$, and $R^7$ each independently represent a hydrogen atom or a methyl group, and $X^1$, $X^2$, $X^3$, $X^4$, $X^5$, $X^6$, and $X^7$ each independently represent a linear or branched hydrocarbon group having 8 to 16 carbon atoms, wherein the hydrocarbon group may have a hydrocarbon chain with one or more groups selected from the group consisting of an oxy group (—O—), a sulfide group (—S—), and a phenylene group.

[2] The dental adhesive composition of [1], wherein the dental adhesive composition comprises a polymerizable monomer (B) that is copolymerizable with the phosphoric acid group-containing polymerizable monomer (A).

[3] The dental adhesive composition of [2], wherein the polymerizable monomer (B) comprises at least one selected from the group consisting of a hydrophobic polymerizable monomer (B-1) having no acidic group, and a hydrophilic polymerizable monomer (B-2) having no acidic group.

[4] The dental adhesive composition of any one of [1] to [3], wherein the dental adhesive composition further comprises a polymerization initiator (C).

[5] The dental adhesive composition of [4], wherein the polymerization initiator (C) comprises a photopolymerization initiator (C-1).

[6] The dental adhesive composition of any one of [1] to [5], wherein $R^1$ in the general formula (1), $R^2$ and $R^3$ in the general formula (2), and $R^4$, $R^5$, $R^6$, and $R^7$ in the general formula (3) are all the same at the same time, and $X^1$ in the general formula (1), $X^2$ and $X^3$ in the general formula (2), and $X^4$, $X^5$, $X^6$, and $X^7$ in the general formula (3) are all the same at the same time.

[7] The dental adhesive composition of any one of [1] to [6], wherein the dental adhesive composition comprises 0.1 to 30.0 parts by mass of the hydrogen phosphate diester group-containing polymerizable monomer (A-2) and 0.05 to 5.0 parts by mass of the phosphoric acid tetraester group-containing polymerizable monomer (A-3) relative to 100 parts by mass of the dihydrogen phosphate monoester group-containing polymerizable monomer (A-1).

Advantageous Effects of Invention

The present invention provides a dental adhesive composition that, even after photocuring with a high-output LED irradiator, shows high bond strength (initial bond strength and bond durability) not only for dentin untreated by phosphoric acid etching but also for dentin treated by phosphoric acid etching.

DESCRIPTION OF EMBODIMENTS

A dental adhesive composition of the present invention comprises a phosphoric acid group-containing polymerizable monomer (A), and the phosphoric acid group-containing polymerizable monomer (A) comprises:

a dihydrogen phosphate monoester group-containing polymerizable monomer (A-1) represented by general formula (1);

a hydrogen phosphate diester group-containing polymerizable monomer (A-2) represented by general formula (2); and a phosphoric acid tetraester group-containing polymerizable monomer (A-3) represented by general formula (3).

[Chem. 1]

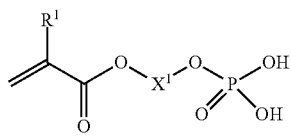

(1)

[Chem. 2]

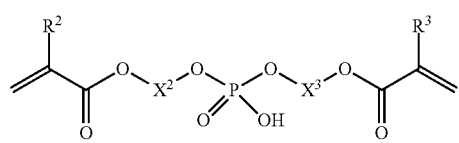

(2)

[Chem. 3]

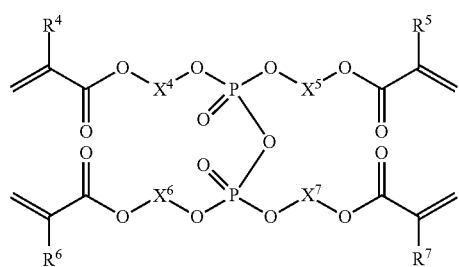

(3)

In the formulae, $R^1$, $R^2$, $R^3$, $R^4$, $R^5$, $R^6$, and $R^7$ each independently represent a hydrogen atom or a methyl group, and $X^1$, $X^2$, $X^3$, $X^4$, $X^5$, $X^6$, and $X^7$ each independently represent a linear or branched hydrocarbon group having 8 to 16 carbon atoms, wherein the hydrocarbon group may have a hydrocarbon chain with one or more groups selected from the group consisting of an oxy group (—O—), a sulfide group (—S—), and a phenylene group.

The term "(meth)acryl" as used in the present specification collectively refers to methacryl and acryl. The same applies to similar expressions. In the present specification, the upper limits and lower limits of numeric ranges (for example, ranges of contents of components, ranges of values calculated from components, and numeric ranges of physical properties) can be combined appropriately.

The dental adhesive composition of the present invention comprising a dihydrogen phosphate monoester group-containing polymerizable monomer (A-1), a hydrogen phosphate diester group-containing polymerizable monomer (A-2), and a phosphoric acid tetraester group-containing polymerizable monomer (A-3) shows high bond strength to dentin subjected to a phosphoric acid etching treatment, even when photocured with a high-output LED irradiator (for example, a light quantity of 1,000 (mW/cm$^2$) or more, preferably 1,500 (mW/cm$^2$) or more). Though the reason for this observation remains unclear, a possible explanation is as follows. In applying a dental adhesive composition to dentin etched with phosphoric acid, the dentin becomes brittle by the strongly demineralizing phosphoric acid etching treatment. It is therefore very important to have the dental adhesive composition penetrate the collagen layer of the embrittled dentin, and impart high mechanical strength upon curing. In a traditional dental adhesive composition containing a dihydrogen phosphate monoester group-containing polymerizable monomer (A-1) and a hydrogen phosphate diester group-containing polymerizable monomer (A-2), the hydrogen phosphate diester group-containing polymerizable monomer (A-2)—a monomer having two polymerizable groups within the molecule—is combined with the dihydrogen phosphate monoester group-containing polymerizable monomer (A-1), which is a monofunctional monomer that serves as a penetrative component, and has low mechanical strength. Though the combination of these components can produce high adhesive property upon curing with a halogen irradiator or a conventional LED irradiator, such a dental adhesive composition lacks sufficient curability by itself when briefly irradiated with a high-output LED irradiator. The phosphoric acid tetraester group-containing polymerizable monomer (A-3) of the present invention has four polymerizable groups within the molecule, and this makes it possible to impart sufficient mechanical strength even with short irradiation. Aside from being highly curable by itself, the phosphoric acid tetraester group-containing polymerizable monomer (A-3) is structurally similar to the dihydrogen phosphate monoester group-containing polymerizable monomer (A-1) and the hydrogen phosphate diester group-containing polymerizable monomer (A-2), and, because of the structural similarity, the phosphoric acid tetraester group-containing polymerizable monomer (A-3) appears to be able to more readily position itself in the vicinity of the polymerizable monomers (A-1) and (A-2) when being cured, enabling more efficient crosslinkage, and formation of a stronger resin-impregnated layer for the embrittled dentin.

The following describes the components used for a dental adhesive composition of the present invention.

Phosphoric Acid Group-Containing Polymerizable Monomer (A)

The phosphoric acid group-containing polymerizable monomer (A) comprises a dihydrogen phosphate monoester group-containing polymerizable monomer (A-1) represented by general formula (1), a hydrogen phosphate diester group-containing polymerizable monomer (A-2) represented by general formula (2), and a phosphoric acid tetraester group-containing polymerizable monomer (A-3) represented by general formula (3).

(i) Dihydrogen Phosphate Monoester Group-Containing Polymerizable Monomer (A-1)

The dihydrogen phosphate monoester group-containing polymerizable monomer (A-1) is a component that imparts demineralizing action and penetrative action with its acid etching effect and priming effect. The dihydrogen phosphate monoester group-containing polymerizable monomer (A-1) is polymerizable, and also imparts a curing effect.

The phosphoric acid group-containing polymerizable monomer (A) comprises a dihydrogen phosphate monoester group-containing polymerizable monomer (A-1) represented by the following general formula (1).

[Chem. 4]

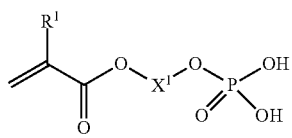
(1)

In the formula, $R^1$ represents a hydrogen atom or a methyl group, and $X^1$ represents a linear or branched hydrocarbon group having 8 to 16 carbon atoms.

Examples of the C8 to C16 hydrocarbon group represented by $X^1$ include saturated hydrocarbon groups and unsaturated hydrocarbon groups. Examples of the C8 to C16 saturated hydrocarbon groups include C8 to C16 alkylene groups. Examples of the unsaturated hydrocarbon groups include C8 to C16 alkenylene groups. The alkylene groups may be linear or branched. Examples of the alkylene groups include an n-octylene group, a 2-ethylhexylene group, an isooctylene group, an n-nonylene group, an n-decylene group, an isodecylene group, an n-decylene group, an n-undecylene group, an isoundecylene group, an n-dodecylene group, an isododecylene group, an n-tridecylene group, an n-tetradecylene group, an n-pentadecylene group, and an n-hexadecylene group. The alkenylene groups may be linear or branched. Examples of the alkenylene groups include an n-octenylene group, an n-nonenylene group, an n-decenylene group, an n-undecenylene group, an n-dodecenylene group, an n-tridecenylene group, an n-tetradecenylene group, an n-pentadecenylene group, and an n-hexadecenylene group. The hydrocarbon group having an alkylene group or an alkenylene group may have a hydrocarbon chain with one or more groups selected from the group consisting of an oxy group (—O—), a sulfide group (—S—), and a phenylene group, or a hydrocarbon chain with one or more groups selected from the group consisting of an oxy group (—O—) and a phenylene group.

The dihydrogen phosphate monoester group-containing polymerizable monomer (A-1) is not particularly limited to specific compounds, and known compounds may be used. In view of storage stability, compounds having a methacryloyl group ($R^1$ in the general formula (1) is a methyl group) are particularly useful.

Specific examples of the dihydrogen phosphate monoester group-containing polymerizable monomer (A-1) include 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, and 16-(meth)acryloyloxyhexadecyl dihydrogen phosphate.

In view of adhesive property for the tooth structure, 10-methacryloyloxydecyl dihydrogen phosphate is most preferred among these dihydrogen phosphate monoester group-containing polymerizable monomers.

The dihydrogen phosphate monoester group-containing polymerizable monomer (A-1) may be used alone, or two or more thereof may be used in combination. Excessively high and low contents of dihydrogen phosphate monoester group-containing polymerizable monomer (A-1) may result in decrease of adhesive property. In this regard, the content of dihydrogen phosphate monoester group-containing polymerizable monomer (A-1) is preferably 1 to 50 parts by mass, more preferably 3 to 40 parts by mass, even more preferably 5 to 30 parts by mass relative to total 100 parts by mass of the polymerizable monomer components in the dental adhesive composition. The bond strength to dentin may decrease with a dihydrogen phosphate monoester group-containing polymerizable monomer (A-1) content of less than 1 part by mass. The mechanical strength of the cured product may decrease with a dihydrogen phosphate monoester group-containing polymerizable monomer (A-1) content of more than 50 parts by mass.

(ii) Hydrogen Phosphate Diester Group-Containing Polymerizable Monomer (A-2)

As with the case of the dihydrogen phosphate monoester group-containing polymerizable monomer (A-1), the hydrogen phosphate diester group-containing polymerizable monomer (A-2) is a component that imparts demineralizing action and penetrative action with its acid etching effect and priming effect. The hydrogen phosphate diester group-containing polymerizable monomer (A-2) is polymerizable, and also imparts a curing effect.

The phosphoric acid group-containing polymerizable monomer (A) comprises a hydrogen phosphate diester group-containing polymerizable monomer (A-2) represented by the following general formula (2).

[Chem. 5]

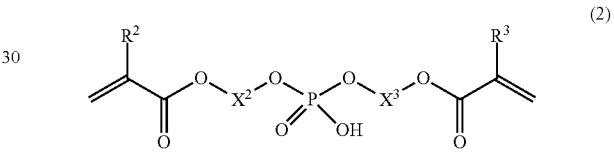
(2)

In the formula, $R^2$ and $R^3$ each independently represent a hydrogen atom or a methyl group, and $X^2$ and $X^3$ each independently represents a linear or branched hydrocarbon group having 8 to 16 carbon atoms. Examples of the C8 to C16 hydrocarbon groups represented by $X^2$ and $X^3$ include saturated hydrocarbon groups and unsaturated hydrocarbon groups. Examples of the C8 to C16 saturated hydrocarbon groups include C8 to C16 alkylene groups. Examples of the unsaturated hydrocarbon groups include C8 to C16 alkenylene groups. The alkylene and alkenylene groups for $X^2$ and $X^3$ are the same as the alkylene and alkenylene groups for X.

The hydrogen phosphate diester group-containing polymerizable monomer (A-2) is not particularly limited to specific compounds, and known compounds may be used. In view of storage stability, compounds having a methacryloyl group ($R^2$ and $R^3$ in the general formula (2) are methyl groups) are particularly useful. Preferred for availability are symmetrical diester compounds ($R^2$ and $R^3$ are the same, and $X^2$ and $X^3$ are the same in the general formula (2)). Particularly preferred are compounds having the same hydrocarbon group structure as the dihydrogen phosphate monoester group-containing polymerizable monomer (A-1) ($R^1$ in the general formula (1), and $R^2$ and $R^3$ in the general formula (2) are all the same, and $X^1$ in the general formula (1), and $X^2$ and $X^3$ in the general formula (2) are all the same) because such compounds enable efficient crosslinkage with the dihydrogen phosphate monoester group-containing polymerizable monomer (A-1), and formation of a stronger resin-impregnated layer for the embrittled dentin after the phosphoric acid etching treatment.

Specific examples of the hydrogen phosphate diester group-containing polymerizable monomer (A-2) include bis [8-(meth)acryloyloxyoctyl]hydrogen phosphate, bis[9-(meth)acryloyloxynonyl]hydrogen phosphate, bis[10-(meth)acryloyloxydecyl]hydrogen phosphate, bis[11-(meth) acryloyloxyundecyl]hydrogen phosphate, bis[12-(meth) acryloyloxydodecyl]hydrogen phosphate, and bis[16-(meth) acryloyloxyhexadecyl]hydrogen phosphate.

Of these compounds, bis[10-(meth)acryloyloxydecyl]hydrogen phosphate is most preferred in view of adhesive property for the tooth structure, and polymerizability and curability.

The hydrogen phosphate diester group-containing polymerizable monomer (A-2) may be used alone, or two or more thereof may be used in combination. The content of hydrogen phosphate diester group-containing polymerizable monomer (A-2) is not particularly limited. However, in view of properties such as the adhesive property of the dental adhesive composition obtained and its polymerizability and curability, the content of hydrogen phosphate diester group-containing polymerizable monomer (A-2) is preferably 0.1 parts by mass to 30 parts by mass, more preferably 0.2 parts by mass to 10 parts by mass, even more preferably 0.5 parts by mass to 3 parts by mass relative to 100 parts by mass of the dihydrogen phosphate monoester group-containing polymerizable monomer (A-1). The bond strength to enamel may decrease with a hydrogen phosphate diester group-containing polymerizable monomer (A-2) content of less than 0.1 parts by mass. The bond strength to dentin may decrease with a hydrogen phosphate diester group-containing polymerizable monomer (A-2) content of more than 30 parts by mass.

(iii) Phosphoric Acid Tetraester Group-Containing Polymerizable Monomer (A-3)

Unlike the dihydrogen phosphate monoester group-containing polymerizable monomer (A-1) and the hydrogen phosphate diester group-containing polymerizable monomer (A-2), the phosphoric acid tetraester group-containing polymerizable monomer (A-3) is a neutral compound, and does not have the acid etching effect and priming effect, and does not impart demineralizing and penetrative action. However, the phosphoric acid tetraester group-containing polymerizable monomer (A-3) has four polymerizable groups within the molecule, and shows high curability by itself. The phosphoric acid tetraester group-containing polymerizable monomer (A-3) is also structurally similar to the dihydrogen phosphate monoester group-containing polymerizable monomer (A-1) and the hydrogen phosphate diester group-containing polymerizable monomer (A-2), and, because of the structural similarity, the phosphoric acid tetraester group-containing polymerizable monomer (A-3) is able to more readily position itself in the vicinity of the polymerizable monomers (A-1) and (A-2) when being cured, enabling more efficient crosslinkage, and formation of a stronger resin-impregnated layer for the embrittled dentin after the phosphoric acid etching treatment.

The phosphoric acid group-containing polymerizable monomer (A) comprises a phosphoric acid tetraester group-containing polymerizable monomer (A-3) represented by the following general formula (3).

[Chem. 6]

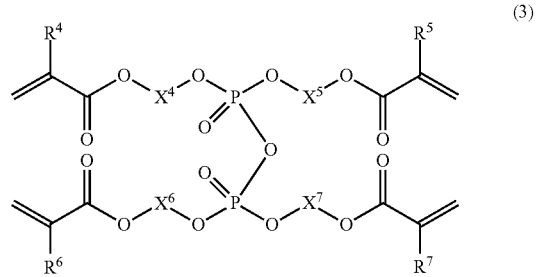

(3)

In the formula, $R^4$, $R^5$, $R^6$, and $R^7$ each independently represent a hydrogen atom or a methyl group, and $X^4$, $X^5$, $X^6$, and $X^7$ each independently represent a linear or branched hydrocarbon group having 8 to 16 carbon atoms. Examples of the C8 to C16 hydrocarbon groups represented by $X^4$, $X^5$, $X^6$, and $X^7$ include saturated hydrocarbon groups and unsaturated hydrocarbon groups. Examples of the C8 to C16 saturated hydrocarbon groups include C8 to C16 alkylene groups. Examples of the unsaturated hydrocarbon groups include C8 to C16 alkenylene groups. The alkylene and alkenylene groups for $X^4$, $X^5$, $X^6$, and $X^7$ are the same as the alkylene and alkenylene groups for $X^1$.

The phosphoric acid tetraester group-containing polymerizable monomer (A-3) is not particularly limited to specific compounds, and known compounds may be used. In view of storage stability, compounds having a methacryloyl group ($R^4$, $R^5$, $R^6$, and $R^7$ in the general formula (3) are methyl groups) are particularly useful. Preferred for availability are symmetrical tetraester compounds ($R^4$, $R^5$, $R^6$, and $R^7$ in the general formula (3) are all the same at the same time, and $X^4$, $X^5$, $X^6$, and $X^7$ in the general formula (3) are all the same at the same time). Particularly preferred are compounds having the same hydrocarbon group structure as the dihydrogen phosphate monoester group-containing polymerizable monomer (A-1) and the hydrogen phosphate diester group-containing polymerizable monomer (A-2) ($R^1$ in the general formula (1), $R^2$ and $R^3$ in the general formula (2), and $R^4$, $R^5$, $R^6$, and $R^7$ in the general formula (3) are all the same at the same time, and $X^1$ in the general formula (1), $X^2$ and $X^3$ in the general formula (2), and $X^4$, $X^5$, $X^6$, and $X^7$ in the general formula (3) are all the same at the same time) because such compounds enable efficient crosslinkage, and formation of an even stronger resin-impregnated layer for the embrittled dentin after the phosphoric acid etching treatment.

Specific examples of the phosphoric acid tetraester group-containing polymerizable monomer (A-3) include tetrakis [8-(meth)acryloyloxyoctyl]phosphate, tetrakis[9-(meth)acryloyloxynonyl]phosphate, tetrakis[10-(meth) acryloyloxydecyl]phosphate, tetrakis[11-(meth) acryloyloxyundecyl]phosphate, tetrakis[12-(meth) acryloyloxydodecyl]phosphate, and tetrakis[16-(meth) acryloyloxyhexadecyl]phosphate.

Of these compounds, tetrakis[10-(meth)acryloyloxydecyl]phosphate is most preferred in view of polymerizability and curability.

The phosphoric acid tetraester group-containing polymerizable monomer (A-3) may be used alone, or two or more thereof may be used in combination. The content of phosphoric acid tetraester group-containing polymerizable monomer (A-3) is not particularly limited. However, in view of properties such as the polymerizability and curability of the dental adhesive composition obtained, the content of phosphoric acid tetraester group-containing polymerizable monomer (A-3) is preferably 0.05 to 5 parts by mass, more preferably 0.1 to 3.0 parts by mass, even more preferably 0.2 to 1.0 parts by mass relative to 100 parts by mass of the dihydrogen phosphate monoester group-containing polymerizable monomer (A-1). The bond strength to enamel may decrease with a phosphoric acid tetraester group-containing polymerizable monomer (A-3) content of less than 0.05 parts by mass. The bond strength to dentin may decrease with a phosphoric acid tetraester group-containing polymerizable monomer (A-3) content of more than 5 parts by mass. Preferably, the content of phosphoric acid tetraester group-containing polymerizable monomer (A-3) is lower than the content of hydrogen phosphate diester group-containing polymerizable monomer (A-2) because this produces high initial bond strength and bond durability for dentin subjected to a phosphoric acid etching treatment even after photocuring with a high-output LED irradiator. Preferably, the content of phosphoric acid tetraester group-containing polymerizable monomer (A-3) is 0.5 to 80 parts by mass relative to 100 parts by mass of the hydrogen phosphate diester group-containing polymerizable monomer (A-2). The content of phosphoric acid tetraester group-containing polymerizable monomer (A-3) is more preferably 1.5 to 70 parts by mass, even more preferably 2.5 to 50 parts by mass because this produces even higher initial bond strength and bond durability for dentin subjected to a phosphoric acid etching treatment even after photocuring with a high-output LED irradiator.

Essentially, the hydrogen phosphate diester group-containing polymerizable monomer (A-2) and the phosphoric acid tetraester group-containing polymerizable monomer (A-3) correspond to by-products of the synthesis of the dihydrogen phosphate monoester group-containing polymerizable monomer (A-1). For example, the hydrogen phosphate diester group-containing polymerizable monomer (A-2) and phosphoric acid tetraester group-containing polymerizable monomer (A-3) generate as a result of dehydrocondensation reaction of the dihydrogen phosphate monoester group-containing polymerizable monomer (A-1) produced in the reaction of hydroxyalkyl (meth)acrylate with phosphorus oxychloride in the presence of an amine compound.

Polymerizable Monomer (B)

In view of adhesive property and mechanical strength, a dental adhesive composition of the present invention preferably comprises a polymerizable monomer (B) that is copolymerizable with the phosphoric acid group-containing polymerizable monomer (A). The polymerizable monomer (B) may be a known polymerizable monomer. Examples of the polymerizable monomer (B) include a hydrophobic polymerizable monomer (B-1) having no acidic group, and a hydrophilic polymerizable monomer (B-2) having no acidic group. The polymerizable monomer (B) may be used alone, or two or more thereof may be used in combination. For example, the hydrophobic polymerizable monomer (B-1) having no acidic group and the hydrophilic polymerizable monomer (B-2) having no acidic group may be used in combination.

(i) Hydrophobic Polymerizable Monomer (B-1) Having no Acidic Group With a dental adhesive composition of the present invention comprising a hydrophobic polymerizable monomer (B-1) having no acidic group, it is possible to improve properties of the cured product (the product resulting from curing of the dental adhesive composition), including mechanical strength, and ease of handling. Preferred as the hydrophobic polymerizable monomer (B-1) having no acidic group are radical polymerizable monomers having no acidic group but having a polymerizable group. For advantages such as ease of radical polymerization, the polymerizable group is preferably a (meth)acryloyl group or a (meth)acrylamide group. The hydrophobic polymerizable monomer (B-1) having no acidic group may be one having a solubility of less than 10 mass % in water at 25° C. Examples of such hydrophobic polymerizable monomers (B-1) having no acidic group include crosslinkable polymerizable monomers, for example, such as aromatic bifunctional monomers, aliphatic bifunctional monomers, and tri- and higher-functional monomers.

Examples of the aromatic bifunctional monomers include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyhenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane.

Preferred among these are 2,2-bis[4-(3-methacryloyloxy-2-hydroxypropoxy)phenyl]propane), 2,2-bis(4-(meth)acryloyloxyethoxyphenyl)propane, 2,2-bis(4-methacryloyloxypolyethoxyphenyl)propane (a compound in which the average number of moles of ethoxy group added is 2.6), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, and 2,2-bis(4-(meth)acryloyloxypentaethoxyphenyl)propane, more preferably 2,2-bis[4-(3-methacryloyloxy-2-hydroxypropoxy)phenyl]propane, and 2,2-bis(4-methacryloyloxypolyethoxyphenyl)propane (a compound in which the average number of moles of ethoxy group added is 2.6).

Examples of the aliphatic bifunctional monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylene bis(2-carbamoyloxyethyl) di(meth)acrylate, N-methacryloyloxyethylacrylamide, N-methacryloyloxypropylacrylamide, N-methacryloyloxybutylacrylamide, N-(1-ethyl-(2-methacryloyloxy)ethyl)acrylamide, and N-(2-(2-methacryloyloxyethoxy)ethyl)acrylamide. Preferred among these are glycerol di(meth)acrylate, triethylene glycol di(meth)acrylate, neopentyl glycol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylene bis(2-carbamoyloxyethyl) di(meth)acrylate, N-methacryloyloxyethylacrylamide, and N-methacryloyloxypropylacrylamide.

Examples of the tri- and higher functional monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dip entaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxyheptane. Preferred among these is N,N-(2,2,4-trimethylhexamethylene)bis[2-(aminocarboxy)propane-1,3-diol]tetra(meth)acrylate.

In view of the mechanical strength and ease of handling of the cured product, the hydrophobic polymerizable monomer (B-1) having no acidic group is preferably an aromatic bifunctional monomer or an aliphatic bifunctional monomer. In view of bond strength, and the mechanical strength of the cured product, the hydrophobic polymerizable monomer (B-1) having no acidic group is more preferably 2,2-bis[4-(3-methacryloyloxy-2-hydroxypropoxy)phenyl]propane, 2,2-bis(4-methacryloyloxypolyethoxyphenyl)propane (a compound in which the average number of moles of ethoxy group added is 2.6), triethylene glycol dimethacrylate, 2,2,4-trimethylhexamethylene bis(2-carbamoyloxyethyl)dimethacrylate, or N-methacryloyloxyethylacrylamide, even more preferably 2,2-bis[4-(3-methacryloyloxy-2-hydroxypropoxy)phenyl]propane, triethylene glycol dimethacrylate, 2,2,4-trimethylhexamethylene bis(2-carbamoyloxyethyl)dimethacrylate, or N-methacryloyloxyethylacrylamide. The hydrophobic polymerizable monomer (B-1) having no acidic group may be used alone, or two or more thereof may be used in combination.

In view of advantages such as improvement of bond strength, the content of the hydrophobic polymerizable monomer (B-1) having no acidic group in a dental adhesive composition of the present invention is preferably at least 9 parts by mass, more preferably at least 15 parts by mass, even more preferably at least 20 parts by mass, particularly preferably at least 30 parts by mass relative to total 100 parts by mass of the polymerizable monomer components contained in the dental adhesive composition. In view of advantages such as improvement of bond strength through improved penetrability into the tooth structure, the content of the hydrophobic polymerizable monomer (B-1) having no acidic group in a dental adhesive composition of the present invention is preferably at most 90 parts by mass, more preferably at most 80 parts by mass, even more preferably at most 75 parts by mass, particularly preferably at most 70 parts by mass relative to total 100 parts by mass of the polymerizable monomer components contained in the dental adhesive composition.

(ii) Hydrophilic Polymerizable Monomer (B-2) Having No Acidic Group

With a dental adhesive composition of the present invention comprising a hydrophilic polymerizable monomer (B-2) having no acidic group, the components of the dental adhesive composition can penetrate the tooth structure in an accelerated fashion while ensuring that the hydrophilic polymerizable monomer (B-2) itself can penetrate into the tooth structure and bind to the organic components (e.g., collagen) in the tooth structure. The hydrophilic polymerizable monomer (B-2) having no acidic group is preferably a radical polymerizable monomer having no acidic group but having a polymerizable group. For advantages such as ease of radical polymerization, the polymerizable group is preferably a (meth)acryloyl group or a (meth)acrylamide group. The hydrophilic polymerizable monomer (B-2) having no acidic group may be one having a solubility of 10 mass % or more in water at 25° C., more preferably one having a solubility of 30 mass % or more in water at 25° C., even more preferably one that can dissolve in water at 25° C. in any proportion.

Preferred as the hydrophilic polymerizable monomer (B-2) having no acidic group are those having a hydrophilic group such as a hydroxyl group, an oxymethylene group, an oxyethylene group, an oxypropylene group, or an amide group. Examples of such hydrophilic polymerizable monomers (B-2) having no acidic group include:

(meth)acrylates such as 2-hydroxyethyl(meth)acrylate, 3-hydroxypropyl(meth)acrylate, 2-hydroxypropyl(meth)acrylate, 1,3-dihydroxypropyl(meth)acrylate, 2,3-dihydroxypropyl(meth)acrylate, 2-trimethylammonium ethyl (meth)acryl chloride, and polyethylene glycol di(meth)acrylate (having at least nine oxyethylene groups);

N-substituted (meth)acrylamides such as N-methylol(meth)acrylamide, N-hydroxyethyl(meth)acrylamide, N-methoxymethyl(meth)acrylamide, N-ethoxymethyl(meth)acrylamide, and diacetone(meth)acrylamide;

4-(meth)acryloylmorpholine; and monofunctional (meth)acrylamides, such as N,N-disubstituted (meth)acrylamides represented by the following general formula (4).

[Chem. 7]

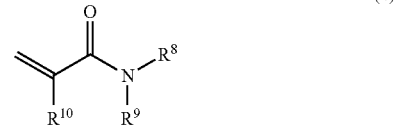

(4)

In the general formula (4), $R^8$ and $R^9$ each independently represent an optionally substituted, linear or branched alkyl group having 1 to 3 carbon atoms, and $R^{10}$ is a hydrogen atom or a methyl group.

Examples of the C1 to C3 alkyl groups independently represented by $R^8$ and RP include a methyl group, an ethyl group, an n-propyl group, and an isopropyl group. Examples of the optional substituents of the alkyl group include a hydroxyl group.

Examples of the N,N-disubstituted (meth)acrylamides represented by the general formula (4) include N,N-dimethyl(meth)acrylamide, N,N-diethyl(meth)acrylamide, and N,N-di(hydroxyethyl)(meth)acrylamide. Preferred in view of properties such as storage stability are N,N-dimethylacrylamide, and N,N-diethylacrylamide, more preferably N,N-diethylacrylamide.

In view of adhesive property for the tooth structure, the hydrophilic polymerizable monomer (B-2) having no acidic group is preferably 2-hydroxyethyl(meth)acrylate, 2,3-dihydroxypropyl(meth)acrylate, or a monofunctional (meth)acrylamide, more preferably 2-hydroxyethyl(meth)acrylate, 2,3-dihydroxypropyl(meth)acrylate, diacetone(meth)acrylamide, or an N,N-disubstituted (meth)acrylamide represented by the general formula (4), even more preferably 2-hydroxyethyl(meth)acrylate, or an N,N-disubstituted (meth)acrylamide represented by the general formula (4), particularly preferably 2-hydroxyethylmethacrylate, or N,N-diethylacrylamide. The hydrophilic polymerizable monomer (B-2) having no acidic group may be used alone, or two or more thereof may be used in combination.

In view of improvement of bond strength through improved penetrability into the tooth structure, the content of the hydrophilic polymerizable monomer (B-2) having no acidic group in a dental adhesive composition of the present invention is preferably at least 9 parts by mass, more preferably at least 15 parts by mass, even more preferably at least 20 parts by mass, particularly preferably at least 30 parts by mass relative to total 100 parts by mass of the polymerizable monomer components. In view of advantages such as improvement of bond strength, the content of the hydrophilic polymerizable monomer (B-2) having no acidic group is preferably at most 90 parts by mass, more preferably at most 80 parts by mass, even more preferably at most 75 parts by mass, particularly preferably at most 70 parts by mass relative to total 100 parts by mass of the polymerizable monomer components.

For advantages such as further improvement of adhesive property for both dental restorative material and tooth structure, the total content of all the polymerizable monomers contained in a dental adhesive composition of the present invention is preferably at least 20 parts by mass, more preferably at least 35 parts by mass, and is preferably at most 90 parts by mass, more preferably at most 80 parts by mass, relative to total 100 parts by mass of the dental adhesive composition.

A dental adhesive composition of the present invention may comprise acidic group-containing polymerizable monomers other than the phosphoric acid group-containing polymerizable monomer (A), provided that such additional acidic group-containing polymerizable monomers do not interfere with the effects of the invention. Examples of acidic group-containing polymerizable monomers other than the phosphoric acid group-containing polymerizable monomer (A) include polymerizable monomers having at least one acidic group such as a phosphoric acid group, a pyrophosphoric acid group, a thiophosphoric acid group, a phosphonic acid group, a sulfonic acid group, or a carboxylic acid group, and having at least one polymerizable group such as an acryloyl group, a methacryloyl group, a vinyl group, or a styrene group. Specific examples of such acidic group-containing polymerizable monomers other than the phosphoric acid group-containing polymerizable monomer (A) are as follows.

Examples of the phosphoric acid group-containing polymerizable monomer include:

dihydrogen phosphate monoester group-containing polymerizable monomers other than the dihydrogen phosphate monoester group-containing polymerizable monomer (A-1), for example, such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, and 20-(meth)acryloyloxyicosyl dihydrogen phosphate;

hydrogen phosphate diester group-containing polymerizable monomers other than the hydrogen phosphate diester group-containing polymerizable monomer (A-2), for example, such as bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl]hydrogen phosphate; and acid chlorides, alkali metal salts, and ammonium salts of these.

Examples of the pyrophosphoric acid group-containing polymerizable monomer include bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts, and ammonium salts of these.

Examples of the thiophosphoric acid group-containing polymerizable monomer include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyicosyl dihydrogen thiophosphate, and acid chlorides, alkali metal salts, and ammonium salts of these.

Examples of the phosphonic acid group-containing polymerizable monomer include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, 10-(meth)acryloyloxydecylphosphonoacetate, and acid chlorides, alkali metal salts, and ammonium salts of these.

Examples of the sulfonic acid group-containing polymerizable monomer include 2-(meth)acrylamide-2-methylpropanesulfonic acid, styrenesulfonic acid, and 2-sulfoethyl (meth)acrylate.

Examples of the carboxylic acid group-containing polymerizable monomer include polymerizable monomers having one carboxy group within the molecule, and polymerizable monomers having a plurality of carboxy groups within the molecule.

Examples of the polymerizable monomers having one carboxy group within the molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and acid halides of these.

Examples of the polymerizable monomers having a plurality of carboxy groups within the molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxidedecane-1,1-dicarboxylic acid, 13-(meth)acryloyloxytridecane-1,1-dicarboxylic acid, 4-(meth)acryloyloxyethyl trimellitate, 4-(meth)acryloyloxyethyl trimellitate anhydride, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, and acid anhydrides or acid halides of these.

Polymerization Initiator (C)

In view of adhesive property, it is preferable that a dental adhesive composition of the present invention further comprise a polymerization initiator (C). The polymerization initiator (C) may be a known polymerization initiator. Examples of the polymerization initiator (C) include a photopolymerization initiator (C-1), and a chemical polymerization initiator (C-2). The polymerization initiator (C) may be used alone, or two or more thereof may be used in combination. For example, the photopolymerization initiator (C-1) and the chemical polymerization initiator (C-2) may be used in combination.

(i) Photopolymerization Initiator (C-1)

Examples of the photopolymerization initiator (C-1) include (bis)acylphosphine oxides (including salts thereof), thioxanthones (including salts such as quaternary ammonium salts), ketals, α-diketones, coumarins, anthraquinones, benzoin alkyl ethers, and α-aminoketone compounds.

Examples of the (bis)acylphosphine oxides include acylphosphine oxides, for example, such as 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di(2,6-dimethylphenyl)phosphonate.

Examples of the (bis)acylphosphine oxides include bisacylphosphine oxides, for example, such as bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyDphenylphosphine oxide, and bis(2,3,6-trimethylbenzoyl)-2,4,4-trimethylpentylphosphine oxide.

The acylphosphine oxides may be water-soluble acylphosphine oxides. Examples of the water-soluble acylphosphine oxides include those having ions, such as alkali metal ions, alkali earth metal ions, pyridinium ions, and ammonium ions, within the acylphosphine oxide molecule. The water-soluble acylphosphine oxides can be synthesized using, for example, the methods disclosed in European Patent Number 0009348, and JP 57(1982)-197289 A.

Specific examples of the water-soluble acylphosphine oxides include monomethyl acetylphosphonate-sodium salt, monomethyl(1-oxopropyl)phosphonate-sodium salt, monomethyl benzoylphosphonate-sodium salt, monomethyl (1-oxobutyl)phosphonate-sodium salt, monomethyl(2-methyl-1-oxopropyl)phosphonate-sodium salt, acetylphosphonate-sodium salt, methyl 4-(hydroxymethoxyphosphinyl)-4-oxobutanoate-sodium salt, methyl 4-oxo-4-phosphonobutanoate-monosodium salt, acetylphenylphosphinate-sodium salt, (1-oxopropyl)pentylphosphinate-sodium salt, methyl 4-(hydroxypentylphosphinyl)-4-oxobutanoate-sodium salt, acetylpentylphosphinate-sodium salt, acetylethylphosphinate-sodium salt, methyl 4-(hydroxymethylphosphinyl)-4-oxobutanoate-lithium salt, 4-(hydroxymethylphosphinyl)-4-oxobutanoic acid-dilithium salt, acetylphosphinate-sodium salt, acetylmethylphosphinate oxime-sodium salt, acetylmethylphosphinate-o-benzyloxime-sodium salt, acetylmethylphosphinate semicarbazone-sodium salt, formylmethyl phosphinate-sodium salt, methyl(1-oxopropyl)phosphinate-sodium salt, acetylmethylphosphinate thiosemicarbazone-sodium salt, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide.

Particularly preferred among these (bis)acylphosphine oxides are 2,4,6-trimethylbenzoyldiphenylphosphine oxide, 2,4,6-trimethylbenzoylmethoxyphenylphosphine oxide, bis (2,4,6-trimethylbenzoyl)phenylphosphine oxide, and sodium salts of 2,4,6-trimethylbenzoylphenylphosphine oxide.

Examples of the thioxanthones include thioxanthone, 2-chlorothioxanthen-9-one, 2-hydroxy-3-(9-oxo-9H-thioxanthen-4-yloxy)-N,N,N-trimethylpropaneaminium chloride, 2-hydroxy-3(1-methyl-9-oxo-9H-thioxanthen-4-yloxy)-N,N,N-trimethyl-1-propaneaminium chloride, 2-hydroxy-3-(9-oxo-9H-thioxanthen-2-yloxy)-N,N,N-trimethyl-1-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminum nium chloride, and 2-hydroxy-3-(1,3,4-trimethyl-9-oxo-9H-thioxanthen-2-yloxy)-N,N,N-trimethyl-1-prop aneaminium chloride.

Preferred among these thioxanthones are 2-chlorothioxanthen-9-one, and 2-hydroxy-3-(3,4-dimethyl-9H-thioxanthen-2-yloxy)-N,N,N-trimethyl-1-propaneami nium chloride.

Examples of the ketals include benzyl dimethyl ketal, and benzyl diethyl ketal.

Examples of the α-diketones include diacetyl, benzyl, DL-camphorquinone, 2,3-pentadione, 2,3-octadione, 9,10-phenanthrenequinone, 4,4'-oxybenzyl, and acenaphthenequinone. Particularly preferred is DL-camphorquinone for its maximum absorption wavelength occurring in the visible light region.

Examples of the coumarins include 3,3'-carbonyl bis(7-diethylaminocoumarin), 3-(4-methoxybenzoyl)coumarin, 3-thienylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3,5-carbonyl bis(7-methoxycoumarin), 3-benzoyl-6-bromocoumarin, 3,3'-carbonyl-bis-coumarin, 3-benzoyl-7-dimethylaminocoumarin, 3-benzoylbenzo[f] coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f] coumarin, 3-benzoyl-6-nitrocoumarin, 3-benzoyl-7-diethylaminocoumarin, 7-dimethylamino-3-(4-methoxybenzoyl) coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f] coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-D]thiazol-2-ylidene)acetyl]coumarin, 3,3'-carbonyl bis(6-methoxycoumarin), 3,3'-carbonyl bis(7-acetoxycoumarin), 3,3'-carbonyl bis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino) coumarin, 3-acetyl-7-(dimethylamino)coumarin, 3,3'-carbonyl bis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6, 7-tetrahydro-1,1,7,7-tetramethyl-1H,5H,11H-[1]benzopyrrano[6,7,8-ij]quinolizin-11-one, and 10-(2-benzothiazoyl)-2,3,6,7-tetrahydro-1,1,7,7-tetramethyl-1H, 5H, 11H-[1]benzopyrrano[6,7,8-ij]quinolizin-11-one.

Preferred among these coumarins are 3,3'-carbonyl bis(7-diethylaminocoumarin), and 3,3'-carbonyl bis(7-dibutylaminocoumarin).

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers include benzoin methyl ether, benzoin ethyl ether, benzoin isopropyl ether, and benzoin isobutyl ether.

Examples of the α-aminoketone compounds include 2-methyl-1-[4-(methylthio)phenyl]2-morpholinopropan-1-one.

The photopolymerization initiator (C-1) is preferably at least one selected from the group consisting of a (bis)acylphosphine oxide, an α-diketone, and a coumarin. In this way, a dental adhesive composition can be provided that has desirable photocurability both in the visible light region and the near ultraviolet region, and that shows sufficient photocurability regardless of whether the light source used is a halogen lamp, a light emitting diode (LED), or a xenon lamp.

(ii) Chemical Polymerization Initiator (C-2)

The chemical polymerization initiator (C-2) may be a known chemical polymerization initiator. Specific examples of the chemical polymerization initiator (C-2) include organic peroxides and inorganic peroxides.

Examples of the organic peroxides include ketone peroxides, hydroperoxides, diacyl peroxides, dialkyl peroxides, peroxyketals, peroxyesters, and peroxydicarbonates. Hydroperoxides and peroxyesters are particularly preferred, and peroxyesters are most preferred for an overall balance of safety, storage stability, and radical generating potential.

Examples of the ketone peroxides include methyl ethyl ketone peroxide, methyl isobutyl ketone peroxide, methylcyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxyesters include α-cumylperoxy neodecanoate, t-butylperoxy neodecanoate, t-butyl peroxypivalate, 2,2,4-trimethylpentylperoxy-2-ethylhexanoate, t-amylperoxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvalerate.

Examples of the peroxydicarbonates include di-3-methoxybutyl peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Examples of the inorganic peroxides include peroxydisulfates and peroxydiphosphates. In view of curability, peroxydisulfates are preferred. Specific examples of the peroxydisulfates include sodium peroxydisulfate, potassium peroxydisulfate, aluminum peroxydisulfate, and ammonium peroxydisulfate.

In view of the bond strength and other properties of the dental adhesive composition obtained, the content of the polymerization initiator (C) in a dental adhesive composition of the present invention is preferably at least 0.01 parts by mass, more preferably at least 0.05 parts by mass, even more preferably at least 0.1 parts by mass relative to total 100 parts by mass of the polymerizable monomer components. In view of the bond strength and other properties of the dental adhesive composition obtained, the content of the polymerization initiator (C) is preferably at most 10 parts by mass relative to total 100 parts by mass of the polymerizable monomer components.

Polymerization Accelerator (D)

The dental adhesive composition of the present invention may further comprise a polymerization accelerator (D). Preferably, the polymerization accelerator (D) is used with the polymerization initiator (C). The polymerization accelerator (D) may be a known polymerization accelerator. Examples of the polymerization accelerator (D) include amines, sulfinic acids (including salts), borate compounds, derivatives of barbituric acid, triazine compounds, copper compounds, tin compounds, vanadium compounds, halogen compounds, aldehydes, thiol compounds, sulfites, bisulfites, and thiourea compounds. The polymerization accelerator (D) may be used alone, or two or more thereof may be used in combination.

The amines can be classified into aliphatic amines and aromatic amines. Examples of the aliphatic amines include primary aliphatic amines such as n-butylamine, n-hexylamine, and n-octylamine; secondary aliphatic amine such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethylmethacrylate, N-methyldiethanolaminedimethacrylate, N-ethyldiethanolaminedimethacrylate, triethanolaminemonomethacrylate, triethanolaminedimethacrylate, triethanolaminetrimethacrylate, triethanolamine, trimethylamine, triethylamine, and tributylamine. In view of the adhesive property and storage stability of the dental adhesive composition, preferred are tertiary aliphatic amines, more preferably N-methyldiethanolamine and triethanolamine.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[meth)acryloyloxy]ethyl 4-(N,N-dimethylamino)benzoate, 4-(N,N-dimethylamino)benzophenone, butyl 4-dimethylaminobenzoate, and 4-(dimethylamino)benzonitrile. In view of the ability to impart desirable adhesive property to the dental adhesive composition, preferred are N,N-di(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone.

Examples of the sulfinic acids include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred are sodium benzenesulfinate, sodium p-toluenesulfinate, and sodium 2,4,6-triisopropylbenzenesulfinate.

The borate compounds are preferably arylborate compounds. Examples of the arylborate compounds include borate compounds having 1 to 4 aryl groups per molecule.

Examples of the borate compounds having one aryl group per molecule include trialkylphenylboron, trialkyl(p-chlorophenyl)boron, trialkyl(p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron, trialkyl(m-octyloxyphenyl)boron (the alkyl group in these compounds is, for example, n-butyl, n-octyl, or n-dodecyl), and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having two aryl groups per molecule include dialkyl diphenylboron, dialkyl di(p-chlorophenyl)boron, dialkyl di(p-fluorophenyl)boron, dialkyl di[3,5-bis(trifluoromethyl)pheny]boron, dialkyl di[3,5-bis(1,1,1,3,3,3-hexafluoro-2-methoxy-2-propyl)phenyl]boron, dialkyl di(p-nitrophenyl)boron, dialkyl di(m-nitrophenyl)boron, dialkyl di(p-butylphenyl)boron, dialkyl di(m-butylphenyl)boron, dialkyl di(p-butyloxyphenyl)boron, dialkyl di(m-butyloxyphenyl)boron, dialkyl di(p-octyloxyphenyl)boron, dialkyl di(m-octyloxyphenyl)boron (the alkyl group in these compounds is, for example, n-butyl, n-octyl, or n-dodecyl), and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having three aryl groups per molecule include monoalkyl triphenylboron, monoalkyl tri(p-chlorophenyl)boron, monoalkyl tri(p-fluorophenyl)boron, monoalkyl tri[3,5-bis(trifluoromethyl)phenyl]boron, monoalkyl tri[3,5-bis(1,1,1,3,3,3-hexafluoro-2-methoxy-2-propyl)phenyl]boron, monoalkyl tri(p-nitrophenyl)boron, monoalkyl tri(m-nitrophenyl)boron, monoalkyl tri(p-butylphenyl)boron, monoalkyl tri(m-butylphenyl)boron, monoalkyl tri(p-butyloxyphenyl)boron, monoalkyl tri(m-butyloxyphenyl)boron, monoalkyl tri(p-octyloxyphenyl)boron, monoalkyl tri(m-octyloxyphenyl) boron (the alkyl group in these compounds is, for example, n-butyl, n-octyl, or n-dodecyl), and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having four aryl groups per molecule include tetraphenylboron, tetrakis(p-chlorophenyl)boron, tetrakis(p-fluorophenyl)boron, tetrakis[3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, (p-octyloxyphenyl)triphenylboron, and salts thereof (e.g., sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

In view of storage stability, preferred as the arylborate compounds are borate compounds having three or four aryl groups per molecule. The arylborate compounds may be used alone, or two or more thereof may be used in combination.

Examples of the derivatives of barbituric acid include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-5-n-butylbarbituric acid, 1,3-dimethyl-5-isobutylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, thiobarbituric acids, and salts thereof. Examples of the salts of derivatives of barbituric acid include alkali metal salts, and alkali-earth metal salts (including magnesium salts), more specifically, sodium 5-butylbarbiturate, sodium 1,3,5-trimethylbarbiturate, and sodium 1-cyclohexyl-5-ethylbarbiturate.

Particularly preferred examples of the derivatives of barbituric acid include 5-butylbarbituric acid, 1,3,5-trimethylbarbituric acid, 1-cyclohexyl-5-ethylbarbituric acid, 1-benzyl-5-phenylbarbituric acid, and sodium salts thereof.

Examples of the triazine compounds include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-α,α,β-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyp henyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Among the triazine compounds exemplified above, 2,4,6-tris(trichloromethyl)-s-triazine is preferred in view of polymerization activity, and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine are preferred in view of storage stability. The triazine compounds may be used alone, or two or more thereof may be used in combination.

Examples of the copper compounds include copper acetylacetonate, copper(II) acetate, copper oleate, copper(II) chloride, and copper(II) bromide.

Examples of the tin compounds include di-n-butyltin dimaleate, di-n-octyltin dimaleate, di-n-octyltin dilaurate, and di-n-butyltin dilaurate. The tin compounds are preferably di-n-octyltin dilaurate and di-n-butyltin dilaurate.

The vanadium compounds are preferably vanadium compounds having a valence of IV and V. Examples of vanadium compounds having a valence of IV and V include vanadium (IV) oxide, vanadium(IV)oxy acetylacetonate, vanadyl oxalate, vanadyl sulfate, vanadium(IV) oxobis(1-phenyl-1,3-butanedionate), bis(maltolato)oxovanadium(IV), vanadium(V) oxide, sodium metavanadate, and ammonium metavanadate.

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde, and derivatives of benzaldehyde. Examples of the derivatives of benzaldehyde include dimethylaminobenzaldehyde, p-methyloxybenzaldehyde, p-ethyloxybenzaldehyde, and p-n-octyloxybenzaldehyde. In view of adhesive property, p-n-octyloxybenzaldehyde is preferred.

Examples of the thiol compounds include 3-mercaptopropyltrimethoxysilane, 2-mercaptobenzooxazole, decanethiol, and thiobenzoic acid.

Examples of the sulfites include sodium sulfite, potassium sulfite, calcium sulfite, and ammonium sulfite.

Examples of the bisulfites include sodium bisulfite and potassium bisulfite.

Examples of the thiourea compounds include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

In view of the bond strength and other properties of the dental adhesive composition obtained, the content of the polymerization accelerator (D) in a dental adhesive composition of the present invention is preferably at least 0.01 parts by mass, more preferably at least 0.05 parts by mass, even more preferably at least 0.1 parts by mass relative to total 100 parts by mass of the polymerizable monomer components. In view of the bond strength and other properties of the dental adhesive composition obtained, the content of the polymerization accelerator (D) is preferably at most 10 parts by mass, more preferably at most 7 parts by mass, even more preferably at most 5 parts by mass relative to total 100 parts by mass of the polymerizable monomer components.

Filler (E)

In certain embodiments, the dental adhesive composition of the present invention may further comprise a filler (E). Typically, the filler (G) can be broadly classified into an organic filler, an inorganic filler, and an organic-inorganic composite filler. Examples of the material of the organic filler include polymethyl methacrylate, polyethyl methacrylate, a methyl methacrylate-ethyl methacrylate copolymer, crosslinked polymethyl methacrylate, crosslinked polyethyl methacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used as a mixture. The shape of the organic filler is not particularly limited, and the organic filler may have an appropriately selected particle diameter. In view of ease of handling, mechanical strength, and other properties of the dental adhesive composition obtained, the organic filler has an average particle diameter of preferably 0.001 to 50 μm, more preferably 0.001 to 10 μm.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone, or two or more thereof may be used in as a mixture. The shape of the inorganic filler is not particularly limited, and the inorganic filler may have an appropriately selected particle diameter. In view of ease of handling, mechanical strength, and other properties of the composition obtained, the inorganic filler has an average particle diameter of preferably 0.001 to 50 μm, more preferably 0.001 to 10 μm.

The inorganic filler may be irregular or spherical in shape. In view of improving the mechanical strength of the composition obtained, the inorganic filler is preferably a spherical filler. Another advantage of using a spherical filler is that it can produce a composite resin having superior surface gloss when a dental adhesive composition of the present invention is used as a self-adhesive dental composite resin. Here, the spherical filler is a filler having an average uniformity of 0.6 or more as calculated for round-shaped particles observed in a unit field of an electron micrograph of the filler, and it is a value obtained by dividing a particle diameter along a direction orthogonal to the maximum diameter by the maximum diameter. The spherical filler has an average particle diameter of preferably 0.05 to 5 μm. An average particle diameter of less than 0.05 μm may result in decrease of the filling rate of the spherical filler in the composition, and decrease of mechanical strength. With an average particle diameter of more than 5 μm, the surface area of the spherical filler may decrease, and the dental adhesive composition may fail to produce a cured product having high mechanical strength.

In order to adjust the flowability of the dental adhesive composition, the inorganic filler may be used after an optional surface treatment with a known surface treatment agent such as a silane coupling agent. Examples of such surface treatment agents include vinyltrimethoxysilane, vinyltriethoxysilane, vinyltrichlorosilane, vinyltri(β-methoxyethoxy)silane, γ-methacryloyloxypropyltrimethoxysilane, 8-methacryloyloxyoctyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is a filler prepared by pulverizing a product of polymerization of a paste-like material prepared by adding a monomer component to the inorganic filler. Examples of the organic-inorganic composite filler include a TMPT filler (a polymerized and pulverized mixture of trimethylolpropanetrimethacrylate and a silica filler). The shape of the organic-inorganic composite filler is not particularly limited, and the organic-inorganic composite filler may have an appropriately selected particle diameter. In view of ease of handling, mechanical strength, and other properties of the composition obtained, the organic-inorganic composite filler has an average particle diameter of preferably 0.001 to 50 μm, more preferably 0.001 to 10 μm.

In the specification, the average particle diameter of the filler is an average primary particle diameter, and can be determined by using a laser diffraction scattering method, or by observing particles with an electron microscope. Specifically, a laser diffraction scattering method is more convenient for particles of 0.1 μm or more, whereas electron microscopy is a more convenient method of particle diameter measurement for ultrafine particles of less than 0.1 μm. Here, 0.1 μm is a measured value by a laser diffraction scattering method.

As a specific example of a laser diffraction scattering method, a laser diffraction particle size distribution analyzer (SALD-2300, manufactured by Shimadzu Corporation) may be used with a 0.2% sodium hexametaphosphate aqueous solution used as a dispersion medium.

As a specific example of electron microscopy, particles may be photographed with an electron microscope (Model S-4000, manufactured by Hitachi), and the size of particles (at least 200 particles) observed in a unit field of the micrograph may be measured using image-analyzing particle-size-distribution measurement software (Macview, manufactured by Mountech Co., Ltd.). Here, the particle diameter is determined as an arithmetic mean value of the maximum and minimum lengths of particles, and the average primary particle diameter is calculated from the number of particles and the particle diameter.

In the present invention, two or more types of fillers differing in material, particle size distribution, and form may be mixed or may be used in combination. Unintentional inclusion of non-filler particles as impurities is acceptable, provided that such particles are not detrimental to the effects of the present invention.

The content of the filler (E) used in the present invention is not particularly limited, and is preferably 0 to 2,000 parts by mass relative to total 100 parts by mass of the polymerizable monomer components in the dental adhesive composition. The preferred content of filler (E) largely depends on the embodiment. The preferred filler (E) contents for different embodiments will be discussed below in conjunction with the descriptions of specific embodiments of the dental adhesive composition of the present invention.

Solvent (F)

In certain embodiments, the dental adhesive composition of the present invention preferably comprises a solvent (F). The solvent may be, for example, water, an organic solvent, or a mixed solvent of these.

In the case where the dental adhesive composition of the present invention comprises water, the water content is preferably 1 to 2,000 parts by mass, more preferably 2 to 1,000 parts by mass, even more preferably 3 to 500 parts by mass relative to total 100 parts by mass of the polymerizable monomer components. Preferably, water is free of adverse impurities. Preferably, water is distilled water or ion-exchange water.

Examples of the organic solvent include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Considering both safety against the body and volatility for ease of removal, the organic solvent is preferably a water-soluble organic solvent, specifically, ethanol, 2-propanol, 2-methyl-2-propanol, acetone, or tetrahydrofuran. The content of the organic solvent is not particularly limited, and, in certain embodiments, addition of the organic solvent may not be necessary. In an embodiment using the organic solvent, the organic solvent content is preferably 1 to 2,000 parts by mass, more preferably 2 to 1,000 parts by mass, even more preferably 3 to 500 parts by mass relative to total 100 parts by mass of the polymerizable monomer components.

Fluorine-Ion Releasing Substance (G)

The dental adhesive composition of the present invention may further comprise a fluorine-ion releasing substance (G). With a fluorine-ion releasing substance (G), a dental adhesive composition can be obtained that can impart acid resistance to the tooth structure. Examples of the fluorine-ion releasing substance (G) include metal fluorides such as sodium fluoride, potassium fluoride, sodium monofluorophosphate, lithium fluoride, and ytterbium fluoride. The fluorine-ion releasing substance (G) may be used alone, or two or more thereof may be used in combination.

The dental adhesive composition may additionally comprise other components, for example, such as a pH adjuster, a polymerization inhibitor, a thickener, a colorant, a fluorescent agent, and a flavor, provided that such additional components do not interfere with the effects of the present invention. The dental adhesive composition may also comprise anti-microbial substances such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, and triclosan. The dental adhesive composition of the present invention may also comprise a polyvalent metal compound (H) to improve bond strength. It is to be noted, however, that a dental adhesive composition of the present invention, even in embodiments not using a polyvalent metal compound (H), can exhibit sufficient bond strength to dentin subjected to a phosphoric acid etching treatment, even after photocuring with a high-output LED irradiator. Examples of the polyvalent metal compound (H) include at least one compound selected from the group consisting of a polyvalent metal alkoxide, a polyvalent metal carbonate, a polyvalent metal hydride, and an alkyl polyvalent metal. Examples of the organic group of the polyvalent metal alkoxide include methylethyl, n-propyl, isopropyl, n-butyl, isobutyl, n-pentyl, n-hexyl, cyclohexyl, n-heptyl, 2-ethylhexyl, and n-octyl. Preferred are alkyl groups having at most four carbon atoms. The alkyl group of the alkyl polyvalent metal is not particularly limited, and may be, for example, an alkyl group having 1 to 20 carbon atoms. Polyvalent metal alkoxides are preferred for their ability to provide high storage stability and improved bond strength. These compounds may be used alone, or two or more thereof may be used in combination. The constituent metallic elements of the polyvalent metal compound are not particularly limited, and may be, for example, the metallic elements in Groups 2 to 13 of the periodic table. However, preferred for desirable bond strength are Group 4 metallic elements, particularly preferably titanium. Specific examples of the polyvalent metal carbonate include calcium carbonate, barium carbonate, aluminum carbonate, lanthanum carbonate, yttrium carbonate, zirconium carbonate, and zinc carbonate. Specific examples of the polyvalent metal hydride include calcium hydride, aluminum hydride, and zirconium hydride. Specific examples of the alkyl polyvalent metal include diethyl magnesium, and trimethyl aluminum.

A dental adhesive composition of the present invention may comprise a known dye or a known pigment.

A dental adhesive composition of the present invention can be used as, for example, a dental primer, a dental bonding material, a self-adhesive dental composite resin, a dental cement, a pit and fissure sealant, a loose tooth fixing material, or an orthodontic adhesive. A dental adhesive composition of the present invention is particularly suited as a dental primer, a dental bonding material, a self-adhesive dental composite resin, or a dental cement. For these applications, a dental adhesive composition of the present invention may be used as a two-part dental adhesive composition of two separate parts. The following describes specific embodiments of different applications of the dental adhesive composition.

Dental Primer

An adhesive system for dental materials includes a demineralization step of dissolving a dentin surface with an acidic component, a penetration step of a monomer component penetrating the collagen layer of dentin, and a curing step of solidifying the penetrated monomer component and forming a hybrid layer (resin-impregnated layer) with collagen. A primer is basically a product used for the penetration step. A newer technique uses a self-etching primer to perform the demineralization and penetration in one step. Because the phosphoric acid group-containing polymerizable monomer (A) has demineralizing action, a dental adhesive composition of the present invention can constitute a self-etching primer with the polymerizable monomer (B) having penetrative action.

A known primer comprising acidic group-containing polymerizable monomers can be used to constitute a dental primer by replacing some or all of the acidic group-containing polymerizable monomers with the phosphoric acid group-containing polymerizable monomer (A) of the present invention (i.e., the phosphoric acid group-containing polymerizable monomer (A) comprising a dihydrogen phosphate monoester group-containing polymerizable monomer (A-1), a hydrogen phosphate diester group-containing polymerizable monomer (A-2), and a phosphoric acid tetraester group-containing polymerizable monomer (A-3)). An example application of the dental adhesive composition as a primer (hereinafter, also referred to simply as "primer composition") is a primer composition comprising the phosphoric acid group-containing polymerizable monomer (A) and the polymerizable monomer (B), and in which the phosphoric acid group-containing polymerizable monomer (A) comprises a dihydrogen phosphate monoester group-containing polymerizable monomer (A-1) represented by general formula (1), a hydrogen phosphate diester group-containing polymerizable monomer (A-2) represented by general formula (2), and a phosphoric acid tetraester group-containing polymerizable monomer (A-3) represented by general formula (3), and the polymerizable monomer (B) comprises a hydrophilic polymerizable monomer (B-2) having no acidic group. Another preferred primer composition is one that further comprises a polymerization initiator (C) and a polymerization accelerator (D), in addition to the components of the primer composition above. In another preferred example, any of the primer compositions above comprises preferably 0.1 to 50 parts by mass of the phosphoric acid group-containing polymerizable monomer (A) and 1 to 99.9 parts by mass of the polymerizable monomer (B), more preferably 0.25 to 30 parts by mass of the phosphoric acid group-containing polymerizable monomer (A) and 10 to 99.75 parts by mass of the polymerizable monomer (B), even more preferably 0.5 to 20 parts by mass of the phosphoric acid group-containing polymerizable monomer (A) and 10 to 99.5 parts by mass of the polymerizable monomer (B), relative to total 100 parts by mass of the polymerizable monomer components. In another preferred example, the primer composition comprising a polymerization initiator (C) and a polymerization accelerator (D) comprises preferably 0.001 to 30 parts by mass of the polymerization initiator (C) and 0.001 to 30 parts by mass of the polymerization accelerator (D), more preferably 0.05 to 20 parts by mass of the polymerization initiator (C) and 0.05 to 20 parts by mass of the polymerization accelerator (D), relative to total 100 parts by mass of the polymerizable monomer components. Preferably, any of the primer compositions above comprises 6 to 3,500 parts by mass, more preferably 7 to 2,000 parts by mass of solvent (F) relative to total 100 parts by mass of the polymerizable monomer components. For purposes such as viscosity adjustments, any of the primer compositions above may comprise 0 to 5 parts by mass of filler (E) relative to total 100 parts by mass of the polymerizable monomer components.

Dental Bonding Material

In a preferred embodiment of the present invention, the dental adhesive composition is used as a dental bonding material. Such a dental bonding material is a bonding material essentially free of water and organic solvent, and that can be used for demineralization, penetration, and curing in one step. As used herein, "essentially free of water and organic solvent" means that the water and organic solvent content is less than 1.0 mass %, preferably less than 0.5 mass %, more preferably less than 0.1 mass %, even more preferably less than 0.01 mass % of the total dental bonding material. The dental bonding material may be a two-part dental bonding material used by mixing two components, A and B, immediately before use, or may be a one-pack type dental bonding material that can be used as it is. For process simplicity, the one-pack type dental bonding material is more advantageous in terms of use. A preferred example of the dental adhesive composition as a dental bonding material (hereinafter, also referred to simply as "dental bonding material") is a composition comprising a phosphoric acid group-containing polymerizable monomer (A), a polymerizable monomer (B), a polymerization initiator (C), a polymerization accelerator (D), and a filler (E), and in which the phosphoric acid group-containing polymerizable monomer (A) comprises a dihydrogen phosphate monoester group-containing polymerizable monomer (A-1) represented by general formula (1), a hydrogen phosphate diester group-containing polymerizable monomer (A-2) represented by general formula (2), and a phosphoric acid tetraester group-containing polymerizable monomer (A-3) represented by general formula (3). In another preferred example, the polymerizable monomer (B) in the dental bonding material above comprises a hydrophobic polymerizable monomer (B-1) having no acidic group. In another preferred example, the polymerizable monomer (B) in any of the dental bonding materials above comprises a hydrophilic polymerizable monomer (B-2) having no acidic group. In another preferred example, the polymerization initiator (C) in any of the dental bonding materials above comprises a photopolymerization initiator (C-1).

The dental bonding material comprises preferably 1 to 90 parts by mass of the phosphoric acid group-containing polymerizable monomer (A) and 1 to 90 parts by mass of the polymerizable monomer (B), more preferably 5 to 80 parts by mass of the phosphoric acid group-containing polymerizable monomer (A) and 5 to 80 parts by mass of the polymerizable monomer (B), relative to total 100 parts by mass of the polymerizable monomer components in the dental adhesive composition. The dental bonding material comprises preferably 0.001 to 30 parts by mass of the polymerization initiator (C), 0.001 to 20 parts by mass of the polymerization accelerator (D), and 0 to 99 parts by mass of the filler (E), more preferably 0.05 to 10 parts by mass of the polymerization initiator (C), 0.05 to 10 parts by mass of the polymerization accelerator (D), and 1 to 50 parts by mass of the filler (E), relative to total 100 parts by mass of the polymerizable monomer components.

Self-Adhesive Dental Composite Resin

Another preferred embodiment of the dental adhesive composition of the present invention is a self-adhesive dental composite resin. Use of a self-adhesive dental composite resin is advantageous because it offers more simplicity than adhesive systems using the dental bonding material, particularly with the recent development of filling composite resins having adhesive property. A preferred example application of the dental adhesive composition as a self-adhesive dental composite resin (hereinafter, also referred to simply as "self-adhesive dental composite resin") is a composition comprising a phosphoric acid group-containing polymerizable monomer (A), a polymerizable monomer (B), a polymerization initiator (C), a polymerization accelerator (D), and a filler (E), and in which the phosphoric acid group-containing polymerizable monomer (A) comprises a dihydrogen phosphate monoester group-containing polymerizable monomer (A-1) represented by general formula (1), a hydrogen phosphate diester group-containing polymerizable monomer (A-2) represented by general formula (2), and a phosphoric acid tetraester group-containing polymerizable monomer (A-3) represented by general formula (3). In another preferred example, the polymerizable monomer (B) in the self-adhesive dental composite resin above comprises a hydrophobic polymerizable monomer (B-1) having no acidic group. In another preferred example, the polymerizable monomer (B) in any of the self-adhesive dental composite resins above comprises a hydrophilic polymerizable monomer (B-2) having no acidic group. In another preferred example, the polymerization initiator (C) in any of the self-adhesive dental composite resins above comprises a photopolymerization initiator (C-1).

The self-adhesive dental composite resin comprises preferably 1 to 90 parts by mass of the phosphoric acid group-containing polymerizable monomer (A) and 1 to 90 parts by mass of the polymerizable monomer (B), more preferably 5 to 80 parts by mass of the phosphoric acid group-containing polymerizable monomer (A) and 5 to 80 parts by mass of the polymerizable monomer (B), relative to total 100 parts by mass of the polymerizable monomer components in the dental adhesive composition. The self-adhesive dental composite resin comprises preferably 0.001 to 30 parts by mass of the polymerization initiator (C), 0.001 to 20 parts by mass of the polymerization accelerator (D), and 51 to 2,000 parts by mass of the filler (E), more preferably 0.05 to 10 parts by mass of the polymerization initiator (C), 0.05 to 10 parts by mass of the polymerization accelerator (D), and 100 to 1,500 parts by mass of the filler (E), relative to total 100 parts by mass of the polymerizable monomer components.

Dental Cement

Another preferred embodiment of the dental adhesive composition of the present invention is a dental cement. Preferred examples of the dental cement include resin cements, and resin-reinforced glass ionomer cements. A self-etching primer, for example, may be used as a pretreatment agent for the dental cement. A preferred example application of the dental adhesive composition as a dental cement (hereinafter, also referred to simply as "dental cement") is a composition comprising a phosphoric acid group-containing polymerizable monomer (A), a polymerizable monomer (B), a polymerization initiator (C), a polymerization accelerator (D), and a filler (E), and in which the phosphoric acid group-containing polymerizable monomer (A) comprises a dihydrogen phosphate monoester group-containing polymerizable monomer (A-1) represented by general formula (1), a hydrogen phosphate diester group-containing polymerizable monomer (A-2) represented by general formula (2), and a phosphoric acid tetraester group-containing polymerizable monomer (A-3) represented by general formula (3).

In another preferred example, the polymerizable monomer (B) in the dental cement above comprises a hydrophobic polymerizable monomer (B-1) having no acidic group. In another preferred example, the polymerizable monomer (B) in any of the dental cements above comprises a hydrophilic polymerizable monomer (B-2) having no acidic group. In another preferred example, the polymerization initiator (C) in any of the dental cements above comprises a chemical polymerization initiator (C-2). Any of the dental cements above may be a two-part dental cement of two separate parts. In this case, it is preferable that the first part mixed with the second part comprise the polymerization initiator (C) (for example, chemical polymerization initiator (C-2)), and the second part mixed with the first part comprise the polymerization accelerator (D).

The dental cement comprises preferably 1 to 90 parts by mass of the phosphoric acid group-containing polymerizable monomer (A) and 1 to 90 parts by mass of the polymerizable monomer (B), more preferably 5 to 80 parts by mass of the phosphoric acid group-containing polymerizable monomer (A) and 5 to 80 parts by mass of the polymerizable monomer (B), relative to total 100 parts by mass of the polymerizable monomer components in the dental adhesive composition. The dental cement comprises preferably 0.001 to 30 parts by mass of the polymerization initiator (C), 0.001 to 20 parts by mass of the polymerization accelerator (D), and 51 to 2,000 parts by mass of the filler (E), more preferably 0.05 to 10 parts by mass of the polymerization initiator (C), 0.05 to 10 parts by mass of the polymerization accelerator (D), and 100 to 1,500 parts by mass of the filler (E), relative to total 100 parts by mass of the polymerizable monomer components.

The present invention encompasses combinations of the foregoing features, provided that such combinations made in various forms within the technical idea of the present invention can produce the effects of the present invention.

EXAMPLES

The following describes the present invention in greater detail by way of Examples. However, the present invention is in no way limited by the following Examples. It should also be noted that the combinations of the features discussed in the Examples below do not necessarily represent all the means necessary for solving the problems identified in the present invention. The components used in the following Examples and Comparative Examples, the abbreviations and the structures of these components are presented below, along with the test methods used.

Phosphoric Acid Group-Containing Polymerizable Monomer (A)
(i) Dihydrogen Phosphate Monoester Group-Containing Polymerizable Monomer
(A-1)
  MDP: 10-Methacryloyloxydecyl dihydrogen phosphate
  MOP: 10-Methacryloyloxyoctyl dihydrogen phosphate
(ii) Hydrogen Phosphate Diester Group-Containing Polymerizable Monomer (A-2)
  Bis-MDP: Bis[10-methacryloyloxydecyl]hydrogen phosphate
  Bis-MOP: Bis[8-methacryloyloxyoctyl]hydrogen phosphate
(iii) Phosphoric Acid Tetraester Group-Containing Polymerizable Monomer (A-3)
  Di-Bis-MDP: Tetrakis[10-methacryloyloxydecyl]phosphate
  Di-Bis-MOP: Tetrakis[8-methacryloyloxyoctyl]phosphate
  Polymerizable Monomer (B)
(i) Hydrophobic Polymerizable Monomer (B-1) Having no Acidic Group
  Bis-GMA: 2,2-Bis[4-(3-methacryloyloxy-2-hydroxypropoxy)phenyl]propane
  D2.6E: 2,2-Bis(4-methacryloyloxypolyethoxyphenyl)propane (a compound in which the average number of moles of ethoxy group added is 2.6)
  UDMA: 2,2,4-Trimethylhexamethylene bis(2-carbamoyloxyethyl)dimethacrylate
  3G: Triethylene glycol dimethacrylate
  MAEA: N-Methacryloyloxyethylacrylamide
  (ii) Hydrophilic Polymerizable Monomer (B-2) Having no Acidic Group
  HEMA: 2-Hydroxyethyl methacrylate
  DEAR: N,N-Diethylacrylamide
  Polymerization Initiator (C)
(i) Photopolymerization Initiator (C-1)
  CQ: DL-Camphorquinone
  BAPO: Bis(2,4,6-trimethylbenzoyl)phenylphosphine oxide
(ii) Chemical Polymerization Initiator (C-1)
  BPB: t-Butyl peroxybenzoate
  BPO: Benzoyl peroxide
  KPS: Potassium peroxydisulfate
  Polymerization Accelerator (D)
  DABE: Ethyl 4-(N,N-dimethylamino)benzoate
  DEPT: N,N-Di(2-hydroxyethyl)-p-toluidine
  TPSS: Sodium 2,4,6-triisopropylbenzenesulfinate
  Filler (E)
Inorganic filler 1: Fine silica particle AEROSIL® R 972 manufactured by Nippon Aerosil Co., Ltd.; average particle diameter: 16 nm
Inorganic filler 2: Fine silica particle AEROSIL® 380 manufactured by Nippon Aerosil Co., Ltd.; average particle diameter: 7 nm
Inorganic filler 3: Aluminum oxide AEROXIDE® AluC manufactured by Nippon Aerosil Co., Ltd.; average particle diameter:13 nm
Inorganic filler 4: Silane-Treated Silica Stone Powder
  A silica stone powder (manufactured by Nitchitsu Co., Ltd. under the trade name Hi-Silica) was pulverized with a ball mill to obtain a pulverized silica stone powder. The pulverized silica stone powder had an average particle diameter of 2.2 μm as measured with a laser diffraction particle size distribution analyzer (Model SALD-2100, manufactured by Shimadzu Corporation). The pulverized silica stone powder was surface treated with 4 parts by mass of γ-methacryloyloxypropyltrimethoxysilane relative to 100 parts by mass of the pulverized silica stone powder, using an ordinary method. This produced a silane-treated silica stone powder.
Inorganic Filler 5: Silane-Treated Barium Glass Powder
  A barium glass (product code E-3000, manufactured by Esstech) was pulverized with a ball mill to obtain a barium glass powder. The barium glass powder had an average particle diameter of 2.4 μm as measured with a laser diffraction particle size distribution analyzer (Model SALD-2100, manufactured by Shimadzu Corporation). The barium glass powder was surface treated with 3 parts by mass of γ-methacryloyloxypropyltrimethoxysilane relative to 100 parts by mass of the barium glass powder, using an ordinary method. This produced a silane-treated barium glass powder.
  Other
  BHT: 2,6-Di-t-butyl-4-methylphenol (stabilizer, polymerization inhibitor)

Synthesis Example 1

Synthesis of Bis-MDP and Di-Bis-MDP
  A 300 mL four-neck flask were charged with 100 mL of THF, 30 g (0.124 moles) of 10-hydroxydecyl methacrylate, and 40 g (0.397 moles) of triethylamine in succession, and the mixture was cooled to −40° C. The solution was then stirred at −30° C. for 3 hours after dropping a 30 mL THF solution of phosphorus oxychloride (9.5 g; 0.062 moles) into the four-neck flask over a time period of 1 hour. After raising the solution temperature to room temperature, the mixture was poured into 200 mL of water, heated to 80° C., and stirred for 5 hours. The solution was then cooled to room temperature, and extracted three times with 150 mL of ethyl acetate. After being dried over magnesium sulfate, the mixture was concentrated under reduced pressure to give an oily crude product, pale brown in color. The product was separated by flash column chromatography, first with dichloromethane, and then with dichloromethane:methanol (9:1 volume ratio), using 300 g of silica gel. The target fractions were then concentrated to give colorless crystals of Bis-MDP (10.1 g) and colorless crystals of Di-Bis-MDP (1.1 g).

Bis-MDP:
$^1$H-NMR (400 MHz, CDCl$_3$): 1.27-1.58 (m,32H), 1.92 (s,6H), 3.52 (D,4H), 4.15 (D,4H), 5.58 (s,2H), 6.15 (s,2H)

Di-Bis-MDP:
$^1$H-NMR (400 MHz, CDCl$_3$): 1.22-1.60 (m,64H), 1.93 (s,12H), 3.53 (D,8H), 4.14 (D,8H), 5.58 (s,4H), 6.15 (s,4H)

Synthesis Example 2

Synthesis of Bis-MOP and Di-Bis-MOP

A 300 mL four-neck flask were charged with 100 mL of THF, 26.6 g (0.124 moles) of 10-hydroxyoctyl methacrylate, and 40 g (0.397 moles) of triethylamine in succession, and the mixture was cooled to –40° C. The solution was then stirred at –30° C. for 3 hours after dropping a 30 mL THF solution of phosphorus oxychloride (9.5 g; 0.062 moles) into the four-neck flask over a time period of 1 hour. After raising the solution temperature to room temperature, the mixture was poured into 200 mL of water, heated to 80° C., and stirred for 5 hours. The solution was then cooled to room temperature, and extracted three times with 150 mL of ethyl acetate. After being dried over magnesium sulfate, the mixture was concentrated under reduced pressure to give an oily crude product, pale brown in color. The product was separated by flash column chromatography, first with dichloromethane, and then with dichloromethane:methanol (9:1 volume ratio), using 300 g of silica gel. The target fractions were then concentrated to give colorless crystals of Bis-MOP (9.1 g) and colorless crystals of Di-Bis-MOP (0.8 g).

Bis-MOP:
$^1$H-NMR (400 MHz, CDCl$_3$): 1.31-1.55 (m,24H), 1.93 (s,6H), 3.53 (D,4H), 4.14 (D,4H), 5.58 (s,2H), 6.15 (s,2H)

Di-Bis-MOP:
$^1$H-NMR (400 MHz, CDCl$_3$): 1.25-1.60 (m,48H), 1.94 (s,12H), 3.51 (D,8H), 4.13 (D,8H), 5.58 (s,4H), 6.15 (s,4H)

Example 1 and Comparative Example 1

Application of Dental Adhesive Composition as Dental Primer

Examples 1-1 to 1-7, and Comparative Examples 1-1 to 1-3

Dental primers of Examples 1-1 to 1-7 and Comparative Examples 1-1 to 1-3 were prepared using the foregoing components, specifically, by mixing and dispersing the components of Table 1 under ordinary temperature. The dental primers were then measured for tensile bond strength to dentin, and dentin cohesive failure rate, using the methods below. Table 1 shows the proportions (parts by mass) of the components of the dental primers of Examples and Comparative Examples, along with the test results.

The labial surfaces of bovine mandibular incisors were ground with #80 silicon carbide paper (manufactured by Nihon Kenshi Co., Ltd.) under running water to obtain samples with an exposed flat dentin surface. Each sample was further ground with #1000 silicon carbide paper (manufactured by Nihon Kenshi Co., Ltd.) under running water. After the completion of grinding, the sample was dried by removing water from its surface by air-blowing.

A dental phosphoric acid etching agent (manufactured by Kuraray Noritake Dental Inc. under the trade name K Etchant Syringe) was applied to the dried, smooth dentin surface by slowly pushing the syringe. After 10 seconds, the dentin was washed with water, and dried. An about 150 μm-thick adhesive tape having a 3 mm circular hole was then attached to the dried smooth dentin surface to define a bonding area.

The dental primers prepared for Examples and Comparative Examples were applied to the circular hole with an applicator brush (manufactured by Kuraray Noritake Dental Inc.; stock number 241-024). After being rubbed for 20 seconds, the surface was dried by blowing air until the applied dental primer was no longer flowable. Thereafter, a commercially available dental bonding material (manufactured by Kuraray Noritake Dental Inc. under the trade name Clearfil® Mega Bond® 2) was applied to form an about 50 μm-thick bond layer over the dried tooth surface coated with the dental primer, using an applicator brush. After application, the dental primer and the dental bonding material were cured by briefly applying light for 3 seconds with a dental LED photoirradiator (manufactured by J. Morita Corp. under the trade name PenCure 2000) in high-output mode (a light quantity of 2,000 (mW/cm$^2$)).

Subsequently, a dental filling composite resin (manufactured by Kuraray Noritake Dental Inc. under the trade name Clearfil® AP-X) was applied to the surface of the cured dental primer and dental bonding material, and a release film (polyester) was placed over the resin. With a glass slide placed on the release film, the surface of the dental filling composite resin was leveled by pressing the glass slide against the release film. The dental filling composite resin was cured by applying light for 20 seconds through the release film, using the irradiator PenCure 2000.

A cylindrical stainless steel rod (measuring 7 mm in diameter and 2.5 cm in length) was bonded at its one end face (circular end face) to the surface of the cured dental filling composite resin, using a commercially available dental resin cement (Panavia® 21, manufactured by Kuraray Noritake Dental Inc.). After bonding, the sample was left to stand at room temperature for 30 minutes, and immersed in distilled water to prepare a sample for adhesion testing. Here, a total of twenty samples were fabricated, and all samples were left to stand in a thermostatic chamber for 24 hours at the maintained temperature of 37° C. In order to evaluate the initial bond strength, ten of the twenty samples were measured for bond strength immediately after the 24-hour storage period. For evaluation of bond durability, the remaining ten samples were measured for bond strength after 4,000 cycles of an alternate thermal process including 1 minute of immersion in 4° C. cold water and 1 minute of immersion in 60° C. hot water.

The samples for adhesion test were measured for tensile bond strength using a universal testing machine (manufactured by Shimadzu Corporation) with a crosshead speed set at 2 mm/min, and the mean value was calculated as the tensile bond strength of the sample.

Dentin Cohesive Failure Rate

For each of the samples for adhesion test subjected to the initial bond strength and bond durability test, the fracture surface was visually inspected, and the fraction (%) of samples that had fracture on the dentin side was calculated as a dentin cohesive failure rate, relative to the total number of samples. Higher dentin cohesive failure rates are suggestive of higher polymerization curability at the bond interface and inside the resin-impregnated layer, meaning that the bond interface has desirable adhesion.

TABLE 1

| Components (parts by mass) | | | Ex. 1-1 | Ex. 1-2 | Ex. 1-3 | Ex. 1-4 | Ex. 1-5 | Ex. 1-6 | Ex. 1-7 | Com. Ex. 1-1 | Com. Ex. 1-2 | Com. Ex. 1-3 |
|---|---|---|---|---|---|---|---|---|---|---|---|---|
| Phosphoric acid group-containing polymerizable monomer (A) | Dihydrogen phosphate monoester group-containing polymerizable monomer (A-1) | MDP MOP | 15 | 15 | 15 | 15 | 5 | 30 | 15 | 15 | 15 | 15 |
| | Hydrogen phosphate diester group-containing polymerizable monomer (A-2) | Bis-MDP Bis-MOP | 0.4 | 0.2 | 1 | 4 | 0.1 | 1.5 | 0.5 | 0 | 0.4 | 0 |
| | Phosphoric acid tetraester group-containing polymerizable monomer (A-3) | Di-Bis-MDP Di-Bis-MOP | 0.01 | 0.05 | 0.5 | 0.7 | 0.005 | 0.1 | 0.2 | 0 | 0 | 0.02 |
| Content of (A-2) relative to 100 parts by mass of (A-1) (parts by mass) | | | 2.67 | 1.33 | 6.67 | 26.67 | 2.00 | 5.00 | 3.33 | 0.00 | 2.67 | 0.00 |
| Content of (A-3) relative to 100 parts by mass of (A-1) (parts by mass) | | | 0.07 | 0.33 | 3.33 | 4.67 | 0.10 | 0.33 | 1.33 | 0.00 | 0.00 | 0.13 |
| Polymerizable monomer (B) | Hydrophilic polymerizable monomer (B-2) having no acidic group | HEMA | 45 | 45 | 45 | 45 | 45 | 45 | 45 | 45 | 45 | 45 |
| Polymerization initiator (C) | Photopolymerization initiator (C-1) | CQ | 0.5 | 0.5 | 0.5 | 0.5 | 0.5 | 0.5 | 0.5 | 0.5 | 0.5 | 0.5 |
| Polymerization accelerator (D) | | DABE | 0.5 | 0.5 | 0.5 | 0.5 | 0.5 | 0.5 | 0.5 | 0.5 | 0.5 | 0.5 |
| Polymerization inhibitor | | BHT | 0.05 | 0.05 | 0.05 | 0.05 | 0.05 | 0.05 | 0.05 | 0.05 | 0.05 | 0.05 |
| Solvent (F) | | Water | 40 | 40 | 40 | 40 | 40 | 40 | 40 | 40 | 40 | 40 |
| Initial bond strength | Tensile bond strength to dentin (MPa) | | 21 | 22 | 20 | 18 | 18 | 18 | 16 | 11 | 12 | 12 |
| | Dentin cohesive failure rate (%) | | 100 | 100 | 80 | 70 | 70 | 70 | 60 | 10 | 10 | 10 |
| Bond durability | Tensile bond strength to dentin (MPa) | | 20 | 21 | 18 | 17 | 16 | 15 | 14 | 8 | 9 | 9 |
| | Dentin cohesive failure rate (%) | | 40 | 40 | 40 | 40 | 40 | 40 | 40 | 0 | 0 | 0 |

As shown in Table 1, the dental primers according to the present invention (Examples 1-1 to 1-7) had initial bond strength with a tensile bond strength of 16 MPa or more, and bond durability with a tensile bond strength of 14 MPa or more for dentin treated by phosphoric acid etching, despite that light was applied only briefly for 3 seconds using a high-output LED. The dental primers according to the present invention had dentin cohesive failure rates with an initial bond strength of 60% or more, and a bond durability of 40% or more, suggesting that the polymerization curability is high at the bond interface and inside the resin-impregnated layer. In contrast, the dental primers (Comparative Examples 1-1 to 1-3) that did not contain the hydrogen phosphate diester group-containing polymerizable monomer (A-2) and/or the phosphoric acid tetraester group-containing polymerizable monomer (A-3) had an initial bond strength of 12 MPa or less, and a bond durability of 9 MPa or less for dentin. As for the dentin cohesive failure rate, the dental primers of Comparative Examples 1-1 to 1-3 had an initial bond strength of 10% or less, and the bond durability was 0%, confirming that the polymerization curability was insufficient at the bond interface and inside the resin-impregnated layer.

Example 2 and Comparative Example 2

Application of Dental Adhesive Composition as Dental Bonding Material

Examples 2-1 to 2-8 and Comparative Examples 2-1 to 2-3

One-pack type dental bonding materials of Examples 2-1 to 2-8 and Comparative Examples 2-1 to 2-3 were prepared using the foregoing components, specifically, by mixing and dispersing the components of Table 2 under ordinary temperature. The dental bonding materials were then measured for tensile bond strength to dentin, and dentin cohesive failure rate, using the methods below. Table 2 shows the proportions (parts by mass) of the components of the dental bonding materials of Examples and Comparative Examples, along with the test results.

The labial surfaces of bovine mandibular incisors were ground with #80 silicon carbide paper (manufactured by Nihon Kenshi Co., Ltd.) under running water to obtain samples with an exposed flat dentin surface. Each sample was further ground with #1000 silicon carbide paper (manufactured by Nihon Kenshi Co., Ltd.) under running water. After the completion of grinding, the sample was dried by removing water from its surface by air-blowing.

A dental phosphoric acid etching agent (manufactured by Kuraray Noritake Dental Inc. under the trade name K Etchant Syringe) was applied to the dried smooth dentin surface by slowly pushing the syringe. After 10 seconds, the dentin was washed with water, and dried. An about 150 μm-thick adhesive tape having a 3 mm circular hole was then attached to the dried smooth dentin surface to define a bonding area.

The one-pack type dental bonding materials prepared for Examples and Comparative Examples were applied to the circular hole with an applicator brush (manufactured by Kuraray Noritake Dental Inc.; stock number 241-024). After being rubbed for 10 seconds, the surface was dried by blowing air until the applied one-pack type dental bonding material was no longer flowable. The one-pack type dental bonding material was then cured by briefly applying light for 3 seconds with a dental LED photoirradiator (manufactured by J. Morita Corp. under the trade name PenCure 2000) in high-output mode (a light quantity of 2,000 (mW/cm$^2$)).

Subsequently, a dental filling composite resin (manufactured by Kuraray Noritake Dental Inc. under the trade name Clearfil® AP-X) was applied to the surface of the cured one-pack type dental bonding material, and a release film (polyester) was placed over the resin. With a glass slide placed on the release film, the surface of the dental filling composite resin was leveled by pressing the glass slide against the release film. The dental filling composite resin was cured by applying light for 20 seconds through the release film, using the irradiator PenCure 2000.

A cylindrical stainless steel rod (measuring 7 mm in diameter and 2.5 cm in length) was bonded at its one end face (circular end face) to the surface of the cured dental filling composite resin, using a commercially available dental resin cement (Panavia® 21, manufactured by Kuraray Noritake Dental Inc.). After bonding, the sample was left to stand at room temperature for 30 minutes, and immersed in distilled water to prepare a sample for adhesion testing. Here, a total of twenty samples were fabricated, and all samples were left to stand in water in a thermostatic chamber for 24 hours at the maintained temperature of 37° C. In order to evaluate the initial bond strength, ten of the twenty samples were measured for bond strength immediately after the 24-hour storage period. For evaluation of bond durability, the remaining ten samples were measured for bond strength after 4,000 cycles of an alternate thermal process including 1 minute of immersion in 4° C. cold water and 1 minute of immersion in 60° C. hot water.

The samples for adhesion test were measured for tensile bond strength using a universal testing machine (manufactured by Shimadzu Corporation) with a crosshead speed set at 2 mm/min, and the mean value was calculated as the tensile bond strength of the sample.

Dentin Cohesive Failure Rate

For each of the samples for adhesion test subjected to the initial bond strength and bond durability test, the fracture surface was visually inspected, and the fraction (%) of samples that had fracture on the dentin side was calculated as a dentin cohesive failure rate, relative to the total number of samples. Higher dentin cohesive failure rates are suggestive of higher polymerization curability at the bond interface and inside the resin-impregnated layer, meaning that the bond interface has desirable adhesion.

TABLE 2

| Components (parts by mass) | | | Ex. 2-1 | Ex. 2-2 | Ex. 2-3 | Ex. 2-4 | Ex. 2-5 | Ex. 2-6 | Ex. 2-7 | Ex. 2-8 | Com. Ex. 2-1 | Com. Ex. 2-2 | Com. Ex. 2-3 |
|---|---|---|---|---|---|---|---|---|---|---|---|---|---|
| Phosphoric acid group-containing polymerizable monomer (A) | Dihydrogen phosphate monoester group-containing polymerizable monomer (A-1) | MDP | 10 | 10 | 10 | 10 | 5 | 30 | 10 | | 10 | 10 | 10 |
| | | MOP | | | | | | | | 10 | | | |
| | Hydrogen phosphate diester group-containing polymerizable monomer (A-2) | Bis-MDP | 0.4 | 0.2 | 1 | 2 | 0.1 | 1.5 | 0.4 | | 0 | 0.5 | 0 |
| | | Bis-MOP | | | | | | | | 0.4 | | | |
| | Phosphoric acid tetraester group-containing polymerizable monomer (A-3) | Di-Bis-MDP | 0.01 | 0.05 | 0.5 | 0.5 | 0.005 | 0.1 | 0.02 | | 0 | 0 | 0.2 |
| | | Di-Bis-MOP | | | | | | | | 0.02 | | | |
| Content of (A-2) relative to 100 parts by mass of (A-1) (parts by mass) | | | 4.00 | 2.00 | 10.00 | 20.00 | 2.00 | 5.00 | 4.00 | 4.00 | 0.00 | 5.00 | 0.00 |
| Content of (A-3) relative to 100 parts by mass of (A-1) (parts by mass) | | | 0.10 | 0.50 | 5.00 | 5.00 | 0.10 | 0.33 | 0.20 | 0.20 | 0.00 | 0.00 | 2.00 |
| Polymerizable monomer (B) | Hydrophobic polymerizable monomer (B-1) having no acidic group | Bis-GMA | 40 | 40 | 40 | 40 | 40 | 40 | 20 | 40 | 40 | 40 | 40 |
| | | MAEA | | | | | | | 20 | | | | |
| | Hydrophilic polymerizable monomer (B-2) having no acidic group | HEMA | 20 | 20 | 20 | 20 | 20 | 20 | 10 | 20 | 20 | 20 | 20 |
| | | DEAA | | | | | | | 10 | | | | |
| Polymerization initiator (C) | Photopolymerization initiator (C-1) | BAPO | 1 | 1 | 1 | 1 | 1 | 1 | 1 | 1 | 1 | 1 | 1 |
| | | CQ | 2 | 2 | 2 | 2 | 2 | 2 | 2 | 2 | 2 | 2 | 2 |
| Polymerization accelerator (D) | | DABE | 1 | 1 | 1 | 1 | 1 | 1 | 1 | 1 | 1 | 1 | 1 |

TABLE 2-continued

| Components (parts by mass) | | Ex. 2-1 | Ex. 2-2 | Ex. 2-3 | Ex. 2-4 | Ex. 2-5 | Ex. 2-6 | Ex. 2-7 | Ex. 2-8 | Com. Ex. 2-1 | Com. Ex. 2-2 | Com. Ex. 2-3 |
|---|---|---|---|---|---|---|---|---|---|---|---|---|
| Polymerization inhibitor | BHT | 0.05 | 0.05 | 0.05 | 0.05 | 0.05 | 0.05 | 0.05 | 0.05 | 0.05 | 0.05 | 0.05 |
| Filler (E) | Inorganic filler 1 | 5 | 5 | 5 | 5 | 5 | 5 | 5 | 5 | 5 | 5 | 5 |
| Solvent (F) | Water | 15 | 15 | 15 | 15 | 15 | 15 | 15 | 15 | 15 | 15 | 15 |
|  | Ethanol | 15 | 15 | 15 | 15 | 15 | 15 | 15 | 15 | 15 | 15 | 15 |
| Initial bond strength | Tensile bond strength to dentin (MPa) | 17 | 18 | 17 | 16 | 17 | 16 | 18 | 16 | 9 | 10 | 10 |
|  | Dentin cohesive failure rate (%) | 70 | 80 | 70 | 70 | 60 | 60 | 80 | 60 | 0 | 10 | 10 |
| Bond durability | Tensile bond strength to dentin (MPa) | 16 | 16 | 16 | 15 | 15 | 14 | 17 | 14 | 7 | 9 | 8 |
|  | Dentin cohesive failure rate (%) | 60 | 70 | 60 | 50 | 50 | 50 | 70 | 50 | 0 | 0 | 0 |

As shown in Table 2, the dental bonding materials according to the present invention (Examples 2-1 to 2-8) had initial bond strength with a tensile bond strength of 16 MPa or more, and bond durability with a tensile bond strength of 14 MPa or more for dentin treated by phosphoric acid etching, despite that light was applied only briefly for 3 seconds using a high-output LED. The dental bonding materials according to the present invention had dentin cohesive failure rates with an initial bond strength of 60% or more, and a bond durability of 50% or more, suggesting that the polymerization curability is high at the bond interface and inside the resin-impregnated layer. In contrast, the dental bonding materials (Comparative Examples 2-1 to 2-3) that did not contain the hydrogen phosphate diester group-containing polymerizable monomer (A-2) and/or the phosphoric acid tetraester group-containing polymerizable monomer (A-3) had an initial bond strength of 10 MPa or less, and a bond durability of 9 MPa or less for dentin. As for the dentin cohesive failure rate, the dental bonding materials of Comparative Examples 2-1 to 2-3 had an initial bond strength of 10% or less, and the bond durability was 0%, confirming that the polymerization curability was insufficient at the bond interface and inside the resin-impregnated layer.

Example 3 and Comparative Example 3

Application of Dental Adhesive Composition as Self-Adhesive Dental Composite Resin Examples 3-1 to 3-8 and Comparative Examples 3-1 to 3-3

Self-adhesive dental composite resins of Examples 3-1 to 3-8 and Comparative Examples 3-1 to 3-3 were prepared using the foregoing components, specifically, by mixing and dispersing the components of Table 3 under ordinary temperature. The self-adhesive dental composite resins were then measured for tensile bond strength to dentin, using the methods below. Table 3 shows the proportions (parts by mass) of the components of the self-adhesive dental composite resins of Examples and Comparative Examples, along with the test results.

The labial surfaces of bovine mandibular incisors were ground with #80 silicon carbide paper (manufactured by Nihon Kenshi Co., Ltd.) under running water to obtain samples with an exposed flat dentin surface. Each sample was further ground with #1000 silicon carbide paper (manufactured by Nihon Kenshi Co., Ltd.) under running water. After the completion of grinding, a commercially available dental phosphoric acid etching agent (manufactured by Kuraray Noritake Dental Inc. under the trade name K Etchant Syringe) was applied to the dentin. After 10 seconds, the dentin was washed with water, and dried. An about 150 μm-thick adhesive tape having a 3 mm circular hole was then attached to the dried smooth surface to define a bonding area.

Thereafter, the self-adhesive dental composite resin prepared for each Example and Comparative Example was filled into the circular hole, and a release film (polyester) was placed over the resin. With a glass slide placed on the release film, the surface of the self-adhesive dental composite resin was leveled by pressing the glass slide against the release film. The self-adhesive dental composite resin was cured by briefly applying light for 3 seconds through the release film, using a dental LED photoirradiator (manufactured by J. Morita Corp. under the trade name PenCure 2000) in high-output mode (a light quantity of 2,000 (mW/cm$^2$)).

A cylindrical stainless steel rod (measuring 7 mm in diameter and 2.5 cm in length) was bonded at its one end face (circular end face) to the surface of the cured self-adhesive dental composite resin, using a commercially available dental resin cement (Panavia® 21, manufactured by Kuraray Noritake Dental Inc.). After bonding, the sample was left to stand at room temperature for 30 minutes, and immersed in distilled water to prepare a sample for adhesion testing. Here, a total of twenty samples were fabricated, and all samples were left to stand in water in a thermostatic chamber for 24 hours at the maintained temperature of 37° C. In order to evaluate the initial bond strength, ten of the twenty samples were measured for bond strength immediately after the 24-hour storage period. For evaluation of bond durability, the remaining ten samples were measured for bond strength after 4,000 cycles of an alternate thermal process including 1 minute of immersion in 4° C. cold water and 1 minute of immersion in 60° C. hot water.

The samples for adhesion test were measured for tensile bond strength using a universal testing machine (manufactured by Shimadzu Corporation) with a crosshead speed set at 2 mm/min, and the mean value was calculated as the tensile bond strength of the sample.

Dentin Cohesive Failure Rate

For each of the samples for adhesion test subjected to the initial bond strength and bond durability test, the fracture surface was visually inspected, and the fraction (%) of samples that had fracture on the dentin side was calculated as a dentin cohesive failure rate, relative to the total number of samples. Higher dentin cohesive failure rates are suggestive of higher polymerization curability at the bond interface and inside the resin-impregnated layer, meaning that the bond interface has desirable adhesion.]

TABLE 3

| Components (parts by mass) | | | Ex. 3-1 | Ex. 3-2 | Ex. 3-3 | Ex. 3-4 | Ex. 3-5 | Ex. 3-6 | Ex. 3-7 | Ex. 3-8 | Com. Ex. 3-1 | Com. Ex. 3-2 | Com. Ex. 3-3 |
|---|---|---|---|---|---|---|---|---|---|---|---|---|---|
| Phosphoric acid group-containing polymerizable monomer (A) | Dihydrogen phosphate monoester group-containing polymerizable monomer (A-1) | MDP | 10 | 10 | 10 | 10 | 5 | 20 | 10 | | 10 | 10 | 10 |
| | | MOP | | | | | | | | 10 | | | |
| | Hydrogen phosphate diester group-containing polymerizable monomer (A-2) | Bis-MDP | 0.4 | 0.2 | 1 | 2.5 | 0.1 | 1.5 | 0.4 | | 0 | 0.5 | 0 |
| | | Bis-MOP | | | | | | | | 0.4 | | | |
| | Phosphoric acid tetraester group-containing polymerizable monomer (A-3) | Di-Bis-MDP | 0.02 | 0.05 | 0.3 | 0.5 | 0.005 | 0.1 | 0.02 | | 0 | 0 | 0.2 |
| | | Di-Bis-MOP | | | | | | | | 0.02 | | | |
| Content of (A-2) relative to 100 parts by mass of (A-1) (parts by mass) | | | 4.00 | 2.00 | 10.00 | 25.00 | 2.00 | 7.50 | 4.00 | 4.00 | 0.00 | 5.00 | 0.00 |
| Content of (A-3) relative to 100 parts by mass of (A-1) (parts by mass) | | | 0.20 | 0.50 | 3.00 | 5.00 | 0.10 | 0.50 | 0.20 | 0.20 | 0.00 | 0.00 | 2.00 |
| Polymerizable monomer (B) | Hydrophobic polymerizable monomer (B-1) having no acidic group | Bis-GMA | 30 | 30 | 30 | 30 | 30 | 30 | 30 | 30 | 30 | 30 | 30 |
| | | UDMA | | | | | | | 10 | | | | |
| | | 3G | 30 | 30 | 30 | 30 | 30 | 30 | | 30 | 30 | 30 | 30 |
| | | MAEA | | | | | | | 20 | | | | |
| | Hydrophilic polymerizable monomer (B-2) having no acidic group | HEMA | 30 | 30 | 30 | 30 | 30 | 30 | 20 | 30 | 30 | 30 | 30 |
| | | DEAA | | | | | | | 10 | | | | |
| Polymerization initiator (C) | Photo-polymerization initiator (C-1) | BAPO | | | | | | | | 1 | | | |
| | | CQ | 0.2 | 0.2 | 0.2 | 0.2 | 0.2 | 0.2 | 0.2 | 0.2 | 0.2 | 0.2 | 0.2 |
| Polymerization accelerator (D) | | DABE | 0.4 | 0.4 | 0.4 | 0.4 | 0.4 | 0.4 | 0.4 | 0.4 | 0.4 | 0.4 | 0.4 |
| Polymerization inhibitor | | BHT | 0.05 | 0.05 | 0.05 | 0.05 | 0.05 | 0.05 | 0.05 | 0.05 | 0.05 | 0.05 | 0.05 |
| Filler (E) | | Inorganic filler 2 | 20 | 20 | 20 | 20 | 20 | 20 | 20 | 20 | 20 | 20 | 20 |
| | | Inorganic filler 4 | 280 | 280 | 280 | 280 | 280 | 280 | | 280 | 280 | 280 | 280 |
| | | Inorganic filler 5 | | | | | | | 280 | | | | |
| Initial bond strength | Tensile bond strength to dentin (MPa) | | 14 | 16 | 14 | 13 | 15 | 14 | 16 | 13 | 6 | 7 | 6 |
| | Dentin cohesive failure rate (%) | | 50 | 60 | 50 | 50 | 40 | 40 | 60 | 40 | 0 | 0 | 0 |
| Bond durability | Tensile bond strength to dentin (MPa) | | 13 | 14 | 13 | 12 | 13 | 13 | 15 | 12 | 4 | 5 | 5 |
| | Dentin cohesive failure rate (%) | | 40 | 40 | 40 | 30 | 30 | 40 | 50 | 30 | 0 | 0 | 0 |

As shown in Table 3, the self-adhesive dental composite resins according to the present invention (Examples 3-1 to 3-8) had initial bond strength with a tensile bond strength of 13 MPa or more, and bond durability with a tensile bond strength of 12 MPa or more for dentin treated by phosphoric acid etching, despite that light was applied only briefly for 3 seconds using a high-output LED. The self-adhesive dental composite resins according to the present invention had dentin cohesive failure rates with an initial bond strength of 40% or more, and a bond durability of 30% or more, suggesting that the polymerization curability is high at the bond interface and inside the resin-impregnated layer. In contrast, the self-adhesive dental composite resins (Comparative Examples 3-1 to 3-3) that did not contain the hydrogen phosphate diester group-containing polymerizable monomer (A-2) and/or the phosphoric acid tetraester group-containing polymerizable monomer (A-3) had an initial bond strength of 7 MPa or less, and a bond durability of 5 MPa or less for dentin. In the self-adhesive dental composite resins of Comparative Examples 3-1 to 3-3, the dentin cohesive failure rate was 0% for both initial bond strength and bond durability, confirming that the polymerization curability was insufficient at the bond interface and inside the resin-impregnated layer.

Example 4 and Comparative Example 4

Application of Dental Adhesive Composition as Dental Cement

Examples 4-1 to 4-10 and Comparative Examples 4-1 to 4-3

Two-part dental cements of Examples 4-1 to 4-10 and Comparative Examples 4-1 to 4-3 were prepared using the foregoing components, specifically, by mixing and dispersing the components of Table 4 under ordinary temperature. The dental cements were then measured for tensile bond strength to dentin, using the methods below. Table 4 shows the proportions (parts by mass) of the components of the dental cements of Examples and Comparative Examples, along with the test results.

The labial surfaces of bovine mandibular incisors were ground with #80 silicon carbide paper (manufactured by Nihon Kenshi Co., Ltd.) under running water to obtain samples with an exposed flat dentin surface. Each sample was further ground with #1000 silicon carbide paper (manufactured by Nihon Kenshi Co., Ltd.) under running water. After the completion of grinding, a commercially available dental phosphoric acid etching agent (manufactured by Kuraray Noritake Dental Inc. under the trade name K Etchant Syringe) was applied to the dentin. After 10 seconds, the dentin was washed with water, and dried. An about 150 μm-thick adhesive tape having a 3 mm circular hole was then attached to the dried smooth surface to define a bonding area.

A cement composition prepared as a mixture of a first and a second part was layered on one end surface of a cylindrical stainless steel rod (measuring 7 mm in diameter and 2.5 cm in length) having a circular cross section. With the center of the circular hole being aligned with the center of the cylindrical stainless steel rod, the end surface with the layered dental cement composition was pressed against the circular hole to vertically place the cylindrical stainless steel rod with respect to the tooth surface. The excess dental cement composition around the cylindrical stainless steel rod was removed with an instrument, and the sample was left to stand at room temperature for 30 minutes. The sample was then immersed in distilled water to prepare a sample for adhesion testing. Here, a total of twenty samples were fabricated, and all samples were left to stand in water in a thermostatic chamber for 24 hours at the maintained temperature of 37° C. In order to evaluate the initial bond strength, ten of the twenty samples were measured for bond strength immediately after the 24-hour storage period. For evaluation of bond durability, the remaining ten samples were measured for bond strength after 4,000 cycles of an alternate thermal process including 1 minute of immersion in 4° C. cold water and 1 minute of immersion in 60° C. hot water.

The samples for adhesion test were measured for tensile bond strength using a universal testing machine (manufactured by Shimadzu Corporation) with a crosshead speed set at 2 mm/min, and the mean value was calculated as the tensile bond strength of the sample.

Dentin Cohesive Failure Rate

For each of the samples for adhesion test subjected to the initial bond strength and bond durability test, the fracture surface was visually inspected, and the fraction (%) of samples that had fracture on the dentin side was calculated as a dentin cohesive failure rate, relative to the total number of samples. Higher dentin cohesive failure rates are suggestive of higher polymerization curability at the bond interface and inside the resin-impregnated layer, meaning that the bond interface has desirable adhesion.

TABLE 4

| | Components (parts by mass) | | | Ex. 4-1 | Ex. 4-2 | Ex. 4-3 | Ex. 4-4 | Ex. 4-5 | Ex. 4-6 | Ex. 4-7 |
|---|---|---|---|---|---|---|---|---|---|---|
| First part | Phosphoric acid group-containing polymerizable monomer (A) | Dihydrogen phosphate monoester group-containing polymerizable monomer (A-1) | MDP MOP | 20 | 20 | 20 | 20 | 10 | 40 | 20 |
| | | Hydrogen phosphate diester group-containing polymerizable monomer (A-2) | Bis-MDP Bis-MOP | 1 | 0.4 | 2 | 4 | 0.2 | 3 | 1 |
| | | Phosphoric acid tetraester group-containing polymerizable monomer (A-3) | Di-Bis-MDP Di-Bis-MOP | 0.02 | 0.1 | 0.5 | 1 | 0.01 | 0.2 | 0.05 |
| | | Content of (A-2) relative to 100 parts by mass of (A-1) (parts by mass) | | 5.00 | 2.00 | 10.00 | 20.00 | 2.00 | 7.50 | 5.00 |
| | | Content of (A-3) relative to 100 parts by mass of (A-1) (parts by mass) | | 0.10 | 0.50 | 2.50 | 5.00 | 0.10 | 0.50 | 0.25 |
| | Polymerizable monomer (B) | Hydrophobic polymerizable monomer (B-1) having no acidic group | Bis-GMA | 40 | 40 | 40 | 40 | 40 | 40 | 30 |
| | | | D2.6E | 25 | 25 | 25 | 25 | 25 | 25 | 15 |
| | | | 3G | 15 | 15 | 15 | 15 | 15 | 15 | 10 |
| | | | MAEA | | | | | | | 10 |
| | | Hydrophilic polymerizable monomer (B-2) having no acidic group | HEMA | | | | | | | 10 |
| | | | DEAA | | | | | | | 5 |
| | Polymerization initiator (C) | Photopolymerization initiator (C-1) | CQ | 0.1 | 0.1 | 0.1 | 0.1 | 0.1 | 0.1 | 0.1 |
| | | Chemical polymerization initiator (C-2) | BPB | 0.5 | 0.5 | 0.5 | 0.5 | 0.5 | 0.5 | 0.5 |
| | | | BPO | | | | | | | |
| | | | KPS | | | | | | | |
| | | Polymerization inhibitor | BHT | 0.05 | 0.05 | 0.05 | 0.05 | 0.05 | 0.05 | 0.05 |
| | | Filler (E) | Inorganic filler 1 | 15 | 15 | 15 | 15 | 15 | 15 | 15 |
| | | | Inorganic filler 4 | 215 | 215 | 215 | 215 | 215 | 215 | 215 |
| Second part | Polymerizable monomer (B) | Hydrophobic polymerizable monomer (B-1) having no acidic group | D2.6E | 80 | 80 | 80 | 80 | 80 | 80 | 80 |
| | | | 3G | 20 | 20 | 20 | 20 | 20 | 20 | 20 |
| | Polymerization accelerator (D) | | DABE | 0.1 | 0.1 | 0.1 | 0.1 | 0.1 | 0.1 | 0.1 |
| | | | DEPT | 0.5 | 0.5 | 0.5 | 0.5 | 0.5 | 0.5 | 0.5 |
| | | | TPSS | 3 | 3 | 3 | 3 | 3 | 3 | 3 |

TABLE 4-continued

| | | | | | | | | | |
|---|---|---|---|---|---|---|---|---|---|
| | Polymerization inhibitor | BHT | 0.05 | 0.05 | 0.05 | 0.05 | 0.05 | 0.05 | 0.05 |
| | Filler (E) | Inorganic filler 3 | 10 | 10 | 10 | 10 | 10 | 10 | 10 |
| | | Inorganic filler 5 | 220 | 220 | 220 | 220 | 220 | 220 | 220 |
| Initial bond strength | | Tensile bond strength to dentin (MPa) | 15 | 16 | 14 | 13 | 15 | 13 | 16 |
| | | Dentin cohesive failure rate (%) | 50 | 50 | 40 | 40 | 50 | 40 | 50 |
| Bond durability | | Tensile bond strength to dentin (MPa) | 13 | 14 | 12 | 12 | 13 | 12 | 14 |
| | | Dentin cohesive failure rate (%) | 40 | 50 | 30 | 30 | 50 | 30 | 40 |

| | Components (parts by mass) | | | Ex. 4-8 | Ex. 4-9 | Ex. 4-10 | Com. Ex. 4-1 | Com. Ex. 4-2 | Com. Ex. 4-3 |
|---|---|---|---|---|---|---|---|---|---|
| First part | Phosphoric acid group-containing polymerizable monomer (A) | Dihydrogen phosphate monoester group-containing polymerizable monomer (A-1) | MDP | | 20 | 20 | 20 | 20 | 20 |
| | | | MOP | 20 | | | | | |
| | | Hydrogen phosphate diester group-containing polymerizable monomer (A-2) | Bis-MDP | | 1 | 1 | 0 | 1 | 0 |
| | | | Bis-MOP | 1 | | | | | |
| | | Phosphonic acid tetraester group-containing monomer (A-3) | Di-Bis-MDP | | 0.05 | 0.05 | 0 | 0 | 0.05 |
| | | | Di-Bis-MOP | 0.05 | | | | | |
| | | Content of (A-2) relative to 100 parts by mass of (A-1) (parts by mass) | | | 5.00 | 5.00 | 5.00 | 0.00 | 5.00 | 0.00 |
| | | Content of (A-3) relative to 100 parts by mass of (A-1) (parts by mass) | | | 0.25 | 0.25 | 0.25 | 0.00 | 0.00 | 0.25 |
| | Polymerizable monomer (B) | Hydrophobic polymerizable monomer (B-1) having no acidic group | Bis-GMA | 40 | 40 | 40 | 40 | 40 | 40 |
| | | | D2.6E | 25 | 25 | 25 | 25 | 25 | 25 |
| | | | 3G | 15 | 15 | 15 | 15 | 15 | 15 |
| | | | MAEA | | | | | | |
| | | Hydrophilic polymerizable monomer (B-2) having no acidic group | HEMA | | | | | | |
| | | | DEAA | | | | | | |
| | Polymerization initiator (C) | Photopolymerization initiator (C-1) | CQ | 0.1 | | | 0.1 | 0.1 | 0.1 |
| | | Chemical polymerization initiator (C-2) | BPB | 0.5 | | | 0.5 | 0.5 | 0.5 |
| | | | BPO | | 3 | | | | |
| | | | KPS | | | 2 | | | |
| | Polymerization inhibitor | | BHT | 0.05 | 0.05 | 0.05 | 0.05 | 0.05 | 0.05 |
| | Filler (E) | | Inorganic filler 1 | 15 | 15 | 15 | 15 | 15 | 15 |
| | | | Inorganic filler 4 | 215 | 215 | 215 | 215 | 215 | 215 |
| Second part | Polymerizable monomer (B) | Hydrophobic polymerizable monomer (B-1) having no acidic group | D2.6E | 80 | 80 | 80 | 80 | 80 | 80 |
| | | | 3G | 20 | 20 | 20 | 20 | 20 | 20 |
| | Polymerization accelerator (D) | | DABE | 0.1 | 0.1 | 0.1 | 0.1 | 0.1 | 0.1 |
| | | | DEPT | 0.5 | 0.5 | 0.5 | 0.5 | 0.5 | 0.5 |
| | | | TPSS | 3 | 3 | 3 | 3 | 3 | 3 |
| | Polymerization inhibitor | | BHT | 0.05 | 0.05 | 0.05 | 0.05 | 0.05 | 0.05 |
| | Filler (E) | | Inorganic filler 3 | 10 | 10 | 10 | 10 | 10 | 10 |
| | | | Inorganic filler 5 | 220 | 220 | 220 | 220 | 220 | 220 |
| Initial bond strength | | Tensile bond strength to dentin (MPa) | | 13 | 13 | 15 | 6 | 7 | 6 |
| | | Dentin cohesive failure rate (%) | | 40 | 40 | 40 | 0 | 0 | 0 |
| Bond durability | | Tensile bond strength to dentin (MPa) | | 12 | 12 | 14 | 4 | 5 | 5 |
| | | Dentin cohesive failure rate (%) | | 30 | 30 | 40 | 0 | 0 | 0 |

As shown in Table 4, the dental cements according to the present invention (Examples 4-1 to 4-10) had initial bond strength with a tensile bond strength of 13 MPa or more, and bond durability with a tensile bond strength of 12 MPa or more for dentin treated by phosphoric acid etching, despite that light was applied only briefly for 3 seconds using a high-output LED. The dental cements according to the present invention had dentin cohesive failure rates with an initial bond strength of 40% or more, and a bond durability of 30% or more, suggesting that the polymerization curability is high at the bond interface and inside the resin-impregnated layer. In contrast, the dental cements (Comparative Examples 4-1 to 4-3) that did not contain the hydrogen phosphate diester group-containing polymerizable monomer (A-2) and/or the phosphoric acid tetraester group-containing polymerizable monomer (A-3) had an initial bond strength of 7 MPa or less, and a bond durability of 5 MPa or less for dentin. In the dental cements of Comparative Examples 4-1 to 4-3, the dentin cohesive failure rate was 0% for both initial bond strength and bond durability, confirming that the polymerization curability was insufficient at the bond interface and inside the resin-impregnated layer.

INDUSTRIAL APPLICABILITY

A dental adhesive composition according to the present invention can be suitably used as a dental primer, a dental bonding material, a self-adhesive dental composite resin, or a dental cement in the field of dentistry.

The invention claimed is:

1. A dental adhesive composition, comprising:
a phosphoric acid group-containing polymerizable monomer,
wherein the phosphoric acid group-containing polymerizable monomer comprises:
a dihydrogen phosphate monoester group-containing polymerizable monomer represented by formula (1);
a hydrogen phosphate diester group-containing polymerizable monomer represented by formula (2); and
a phosphoric acid tetraester group-containing polymerizable monomer represented by formula (3),

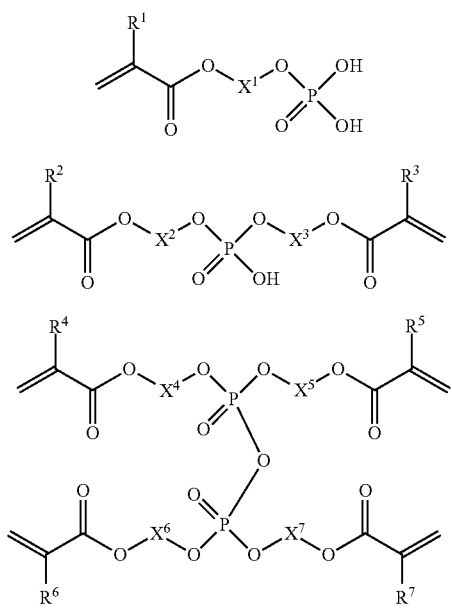

where $R^1$, $R^2$, $R^3$, $R^4$, $R^5$, $R^6$, and $R^7$ each independently represent a hydrogen atom or a methyl group, and $X^1$, $X^2$, $X^3$, $X^4$, $X^5$, $X^6$, and $X^7$ each independently represent a linear or branched hydrocarbon group having 8 to 16 carbon atoms, wherein the hydrocarbon group optionally has a hydrocarbon chain with one or more groups selected from the group consisting of an oxy group, a sulfide group, and a phenylene group.

2. The dental adhesive composition according to claim 1, wherein the dental adhesive composition comprises a polymerizable monomer that is copolymerizable with the phosphoric acid group-containing polymerizable monomer.

3. The dental adhesive composition according to claim 2, wherein the polymerizable monomer comprises at least one selected from the group consisting of a hydrophobic polymerizable monomer having no acidic group, and a hydrophilic polymerizable monomer having no acidic group.

4. The dental adhesive composition according to claim 1, wherein the dental adhesive composition further comprises a polymerization initiator.

5. The dental adhesive composition according to claim 4, wherein the polymerization initiator comprises a photopolymerization initiator.

6. The dental adhesive composition according to claim 1, wherein $R^1$, $R^2$, $R^3$, $R^4$, $R^5$, $R^6$, and $R^7$ are all the same, and $X^1$, $X^2$, $X^3$, $X^4$, $X^5$, $X^6$, and $X^7$ are all the same.

7. The dental adhesive composition according to claim 1, wherein the dental adhesive composition comprises from 0.1 to 30.0 parts by mass of the hydrogen phosphate diester group-containing polymerizable monomer and from 0.05 to 5.0 parts by mass of the phosphoric acid tetraester group-containing polymerizable monomer relative to 100 parts by mass of the dihydrogen phosphate monoester group-containing polymerizable monomer.

* * * * *